US00RE47882E

(19) United States
(12) Reissued Patent
Al-Ali

(10) Patent Number: US RE47,882 E
(45) Date of Reissued Patent: *Mar. 3, 2020

(54) ADAPTIVE ALARM SYSTEM

(71) Applicant: MASIMO Corporation, Irvine, CA (US)

(72) Inventor: Ammar Al-Ali, San Juan Capistrano, CA (US)

(73) Assignee: MASIMO CORPORATION, Irvine, CA (US)

( * ) Notice: This patent is subject to a terminal disclaimer.

(21) Appl. No.: 16/184,908

(22) Filed: Nov. 8, 2018

Related U.S. Patent Documents

Reissue of:

(64) Patent No.: 9,775,570
Issued: Oct. 3, 2017
Appl. No.: 15/583,718
Filed: May 1, 2017

U.S. Applications:

(63) Continuation of application No. 15/881,602, filed on Jan. 26, 2018, now Pat. No. Re. 47,218, which is an (Continued)

(51) Int. Cl.
*A61B 5/00* (2006.01)
*A61B 5/1455* (2006.01)

(52) U.S. Cl.
CPC ..... *A61B 5/746* (2013.01); *A61B 5/1455* (2013.01); *A61B 5/14552* (2013.01); *A61B 5/74* (2013.01)

(58) Field of Classification Search
CPC ... A61B 5/746; A61B 5/1455; A61B 5/14552; A61B 5/74

(Continued)

(56) References Cited

U.S. PATENT DOCUMENTS 4,639,718 A 1/1987 Gasper
4,653,498 A 3/1987 New et al.

(Continued)

FOREIGN PATENT DOCUMENTS

WO WO 03/007815 1/2003
WO WO 03/028549 4/2003

(Continued)

OTHER PUBLICATIONS

US 9,579,050 B2, 02/2017, Al-Ali (withdrawn)

(Continued)

*Primary Examiner* — Beverly M Flanagan
(74) *Attorney, Agent, or Firm* — Knobbe Martens Olson & Bear, LLP

(57) ABSTRACT

Systems and electronic processes for reducing electronic alarms in a medical patient monitoring system. For example, a system for reducing electronic alarms can include an optical sensor and one or more hardware processors in electronic communication with the optical sensor. The one or more hardware processors can be programmed to measure oxygen saturation values of a patient over a first period of time, determine if at least one oxygen saturation value obtained over the first period of time exceeds a first alarm threshold, determine whether a first alarm should be triggered based on the determination that the at least one oxygen saturation value obtained over the first period of time exceeds the first alarm threshold, determine a second alarm threshold to be applied during a second period of time subsequent to the first period of time, the second alarm threshold replacing the first alarm threshold.

17 Claims, 14 Drawing Sheets

Related U.S. Application Data application for the reissue of Pat. No. 9,775,570, which is a continuation of application No. 13/037,184, filed on Feb. 28, 2011, now Pat. No. 9,724,024.

(60) Provisional application No. 61/309,419, filed on Mar. 1, 2010, provisional application No. 61/328,630, filed on Apr. 27, 2010.

(58) Field of Classification Search
USPC ..... 600/300, 301, 310, 322, 323, 324, 473, 600/476, 500, 508; 356/41, 573.1
See application file for complete search history.

(56) References Cited

U.S. PATENT DOCUMENTS 4,960,128 A 10/1990 Gordon et al.
4,964,408 A 10/1990 Hink et al.
5,041,187 A 8/1991 Hink et al.
5,069,213 A 12/1991 Polczynski
5,111,817 A 5/1992 Clark et al.
5,163,438 A 11/1992 Gordon et al.
5,226,417 A 7/1993 Swedlow et al.
5,253,645 A 10/1993 Friedman et al.
5,253,646 A 10/1993 Delpy et al.
5,285,782 A 2/1994 Prosser
5,319,355 A 6/1994 Russek
5,319,363 A 6/1994 Welch
5,337,744 A 8/1994 Branigan
5,341,805 A 8/1994 Stavridi et al.
D353,195 S 12/1994 Savage et al.
D353,196 S 12/1994 Savage et al.
5,377,676 A 1/1995 Vari et al.
D359,546 S 6/1995 Savage et al.
5,431,170 A 7/1995 Mathews
D361,840 S 8/1995 Savage et al.
D362,063 S 9/1995 Savage et al.
5,452,717 A 9/1995 Branigan et al.
D363,120 S 10/1995 Savage et al.
5,456,252 A 10/1995 Vari et al.
5,464,012 A 11/1995 Falcone
5,479,934 A 1/1996 Imran
5,482,036 A 1/1996 Diab et al.
5,490,505 A 2/1996 Diab et al.
5,494,043 A 2/1996 O'Sullivan et al.
5,533,511 A 7/1996 Kaspari et al.
5,534,851 A 7/1996 Russek
5,561,275 A 10/1996 Savage et al.
5,562,002 A 10/1996 Lalin
5,590,649 A 1/1997 Caro et al.
5,602,924 A 2/1997 Durand et al.
5,632,272 A 5/1997 Diab et al.
5,638,816 A 6/1997 Kiani-Azarbayjany et al.
5,638,818 A 6/1997 Diab et al.
5,645,440 A 7/1997 Tobler et al.
5,685,299 A 11/1997 Diab et al.
D393,830 S 4/1998 Tobler et al.
5,743,262 A 4/1998 Lepper, Jr. et al.
5,758,644 A 6/1998 Diab et al.
5,760,910 A 6/1998 Lepper, Jr. et al.
5,769,785 A 6/1998 Diab et al.
5,782,757 A 7/1998 Diab et al.
5,785,659 A 7/1998 Caro et al.
5,791,347 A 8/1998 Flaherty et al.
5,810,734 A 9/1998 Caro et al.
5,823,950 A 10/1998 Diab et al.
5,830,131 A 11/1998 Caro et al.
5,833,618 A 11/1998 Caro et al.
5,860,919 A 1/1999 Kiani-Azarbayjany et al.
5,876,348 A 3/1999 Sugo et al.
5,890,929 A 4/1999 Mills et al.
5,904,654 A 5/1999 Wohltmann et al.
5,919,134 A 7/1999 Diab
5,934,925 A 8/1999 Tobler et al.
5,940,182 A 8/1999 Lepper, Jr. et al.
5,995,855 A 11/1999 Kiani et al.
5,997,343 A 12/1999 Mills et al.
6,002,952 A 12/1999 Diab et al.
6,005,658 A 12/1999 Kaluza et al.
6,011,986 A 1/2000 Diab et al.
6,027,452 A 2/2000 Flaherty et al.
6,036,642 A 3/2000 Diab et al.
6,045,509 A 4/2000 Caro et al.
6,050,951 A 4/2000 Friedman et al.
6,067,462 A 5/2000 Diab et al.
6,081,735 A 6/2000 Diab et al.
6,088,607 A 7/2000 Diab et al.
6,110,522 A 8/2000 Lepper, Jr. et al.
6,124,597 A 9/2000 Shehada
6,128,521 A 10/2000 Marro et al.
6,129,675 A 10/2000 Jay
6,144,868 A 11/2000 Parker
6,151,516 A 11/2000 Kiani-Azarbayjany et al.
6,152,754 A 11/2000 Gerhardt et al.
6,157,850 A 12/2000 Diab et al.
6,165,005 A 12/2000 Mills et al.
6,184,521 B1 2/2001 Coffin, IV et al.
6,190,325 B1 2/2001 Narimatsu
6,206,830 B1 3/2001 Diab et al.
6,229,856 B1 5/2001 Diab et al.
6,232,609 B1 5/2001 Snyder et al.
6,236,872 B1 5/2001 Diab et al.
6,241,661 B1 6/2001 Schluess et al.
6,241,683 B1 6/2001 Macklem et al.
6,253,097 B1 6/2001 Aronow et al.
6,256,523 B1 7/2001 Diab et al.
6,263,222 B1 7/2001 Diab et al.
6,278,522 B1 8/2001 Lepper, Jr. et al.
6,280,213 B1 8/2001 Tobler et al.
6,285,896 B1 9/2001 Tobler et al.
6,301,493 B1 10/2001 Marro et al.
6,317,627 B1 11/2001 Ennen et al.
6,321,100 B1 11/2001 Parker
6,325,761 B1 12/2001 Jay
6,334,065 B1 12/2001 Al-Ali et al.
6,343,224 B1 1/2002 Parker
6,349,228 B1 2/2002 Kiani et al.
6,360,114 B1 3/2002 Diab et al.
6,368,283 B1 4/2002 Xu et al.
6,371,921 B1 4/2002 Caro et al.
6,377,829 B1 4/2002 Al-Ali
6,388,240 B2 5/2002 Schulz et al.
6,397,091 B2 5/2002 Diab et al.
6,430,437 B1 8/2002 Marro
6,430,525 B1 8/2002 Weber et al.
6,463,311 B1 10/2002 Diab
6,470,199 B1 10/2002 Kopotic et al.
6,501,975 B2 12/2002 Diab et al.
6,505,059 B1 1/2003 Kollias et al.
6,515,273 B2 2/2003 Al-Ali
6,519,487 B1 2/2003 Parker
6,525,386 B1 2/2003 Mills et al.
6,526,300 B1 2/2003 Kiani et al.
6,541,756 B2 4/2003 Schulz et al.
6,542,764 B1 4/2003 Al-Ali et al.
6,553,242 B1 4/2003 Sarussi
6,580,086 B1 6/2003 Schulz et al.
6,584,336 B1 6/2003 Ali et al.
6,595,316 B2 7/2003 Cybulski et al.
6,597,932 B2 7/2003 Tian et al.
6,597,933 B2 7/2003 Kiani et al.
6,606,511 B1 8/2003 Ali et al.
6,632,181 B2 10/2003 Flaherty et al.
6,639,668 B1 10/2003 Trepagnier
6,640,116 B2 10/2003 Diab
6,643,530 B2 11/2003 Diab et al.
6,645,155 B2 11/2003 Inukai et al.
6,650,917 B2 11/2003 Diab et al.
6,654,624 B2 11/2003 Diab et al.
6,658,276 B2 12/2003 Kiani et al.
6,661,161 B1 12/2003 Lanzo et al.
6,671,531 B2 12/2003 Al-Ali et al.
6,678,543 B2 1/2004 Diab et al.
6,684,090 B2 1/2004 Ali et al.

(56) References Cited

U.S. PATENT DOCUMENTS

| | | | |
|---|---|---|---|
| 6,684,091 | B2 | 1/2004 | Parker |
| 6,697,656 | B1 | 2/2004 | Al-Ali |
| 6,697,657 | B1 | 2/2004 | Shehada et al. |
| 6,697,658 | B2 | 2/2004 | Al-Ali |
| RE38,476 | E | 3/2004 | Diab et al. |
| 6,699,194 | B1 | 3/2004 | Diab et al. |
| 6,714,804 | B2 | 3/2004 | Al-Ali et al. |
| RE38,492 | E | 4/2004 | Diab et al. |
| 6,721,582 | B2 | 4/2004 | Trepagnier et al. |
| 6,721,585 | B1 | 4/2004 | Parker |
| 6,725,075 | B2 | 4/2004 | Al-Ali |
| 6,728,560 | B2 | 4/2004 | Kollias et al. |
| 6,735,459 | B2 | 5/2004 | Parker |
| 6,745,060 | B2 | 6/2004 | Diab et al. |
| 6,754,516 | B2 | 6/2004 | Mannheimer |
| 6,760,607 | B2 | 7/2004 | Al-Ali |
| 6,770,028 | B1 | 8/2004 | Ali et al. |
| 6,771,994 | B2 | 8/2004 | Kiani et al. |
| 6,792,300 | B1 | 9/2004 | Diab et al. |
| 6,813,511 | B2 | 11/2004 | Diab et al. |
| 6,816,741 | B2 | 11/2004 | Diab |
| 6,822,564 | B2 | 11/2004 | Al-Ali |
| 6,826,419 | B2 | 11/2004 | Diab et al. |
| 6,830,711 | B2 | 12/2004 | Mills et al. |
| 6,850,787 | B2 | 2/2005 | Weber et al. |
| 6,850,788 | B2 | 2/2005 | Al-Ali |
| 6,852,083 | B2 | 2/2005 | Caro et al. |
| 6,861,639 | B2 | 3/2005 | Al-Ali |
| 6,898,452 | B2 | 5/2005 | Al-Ali et al. |
| 6,920,345 | B2 | 7/2005 | Al-Ali et al. |
| 6,931,268 | B1 | 8/2005 | Kiani-Azarbayjany et al. |
| 6,934,570 | B2 | 8/2005 | Kiani et al. |
| 6,939,305 | B2 | 9/2005 | Flaherty et al. |
| 6,943,348 | B1 | 9/2005 | Coffin, IV |
| 6,950,687 | B2 | 9/2005 | Al-Ali |
| 6,961,598 | B2 | 11/2005 | Diab |
| 6,970,792 | B1 | 11/2005 | Diab |
| 6,979,812 | B2 | 12/2005 | Al-Ali |
| 6,985,764 | B2 | 1/2006 | Mason et al. |
| 6,993,371 | B2 | 1/2006 | Kiani et al. |
| 6,996,427 | B2 | 2/2006 | Ali et al. |
| 6,999,904 | B2 | 2/2006 | Weber et al. |
| 7,003,338 | B2 | 2/2006 | Weber et al. |
| 7,003,339 | B2 | 2/2006 | Diab et al. |
| 7,015,451 | B2 | 3/2006 | Dalke et al. |
| 7,024,233 | B2 | 4/2006 | Ali et al. |
| 7,027,849 | B2 | 4/2006 | Al-Ali |
| 7,030,749 | B2 | 4/2006 | Al-Ali |
| 7,039,449 | B2 | 5/2006 | Al-Ali |
| 7,041,060 | B2 | 5/2006 | Flaherty et al. |
| 7,044,918 | B2 | 5/2006 | Diab |
| 7,067,893 | B2 | 6/2006 | Mills et al. |
| 7,096,052 | B2 | 8/2006 | Mason et al. |
| 7,096,054 | B2 | 8/2006 | Abdul-Hafiz et al. |
| 7,123,950 | B2 | 10/2006 | Mannheimer |
| 7,132,641 | B2 | 11/2006 | Schulz et al. |
| 7,142,901 | B2 | 11/2006 | Kiani et al. |
| 7,149,561 | B2 | 12/2006 | Diab |
| 7,186,966 | B2 | 3/2007 | Al-Ali |
| 7,190,261 | B2 | 3/2007 | Al-Ali |
| 7,215,984 | B2 | 5/2007 | Diab |
| 7,215,986 | B2 | 5/2007 | Diab |
| 7,221,971 | B2 | 5/2007 | Diab |
| 7,225,006 | B2 | 5/2007 | Al-Ali et al. |
| 7,225,007 | B2 | 5/2007 | Al-Ali |
| RE39,672 | E | 6/2007 | Shehada et al. |
| 7,239,905 | B2 | 7/2007 | Kiani-Azarbayjany et al. |
| 7,245,953 | B1 | 7/2007 | Parker |
| 7,254,429 | B2 | 8/2007 | Schurman et al. |
| 7,254,431 | B2 | 8/2007 | Al-Ali |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani et al. |
| D554,263 | S | 10/2007 | Al-Ali |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,295,866 | B2 | 11/2007 | Al-Ali |
| 7,328,053 | B1 | 2/2008 | Diab et al. |
| 7,332,784 | B2 | 2/2008 | Mills et al. |
| 7,340,287 | B2 | 3/2008 | Mason et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,355,512 | B1 | 4/2008 | Al-Ali |
| 7,356,365 | B2 | 4/2008 | Schurman |
| 7,371,981 | B2 | 5/2008 | Abdul-Hafiz |
| 7,373,193 | B2 | 5/2008 | Al-Ali et al. |
| 7,373,194 | B2 | 5/2008 | Weber et al. |
| 7,376,453 | B1 | 5/2008 | Diab et al. |
| 7,377,794 | B2 | 5/2008 | Al-Ali et al. |
| 7,377,899 | B2 | 5/2008 | Weber et al. |
| 7,383,070 | B2 | 6/2008 | Diab et al. |
| 7,415,297 | B2 | 8/2008 | Al-Ali et al. |
| 7,428,432 | B2 | 9/2008 | Ali et al. |
| 7,438,683 | B2 | 10/2008 | Al-Ali et al. |
| 7,440,787 | B2 | 10/2008 | Diab |
| 7,454,240 | B2 | 11/2008 | Diab et al. |
| 7,467,002 | B2 | 12/2008 | Weber et al. |
| 7,469,157 | B2 | 12/2008 | Diab et al. |
| 7,471,969 | B2 | 12/2008 | Diab et al. |
| 7,471,971 | B2 | 12/2008 | Diab et al. |
| 7,483,729 | B2 | 1/2009 | Al-Ali et al. |
| 7,483,730 | B2 | 1/2009 | Diab et al. |
| 7,489,958 | B2 | 2/2009 | Diab et al. |
| 7,496,391 | B2 | 2/2009 | Diab et al. |
| 7,496,393 | B2 | 2/2009 | Diab et al. |
| D587,657 | S | 3/2009 | Al-Ali et al. |
| 7,499,741 | B2 | 3/2009 | Diab et al. |
| 7,499,835 | B2 | 3/2009 | Weber et al. |
| 7,500,950 | B2 | 3/2009 | Al-Ali et al. |
| 7,509,154 | B2 | 3/2009 | Diab et al. |
| 7,509,494 | B2 | 3/2009 | Al-Ali |
| 7,510,849 | B2 | 3/2009 | Schurman et al. |
| 7,526,328 | B2 | 4/2009 | Diab et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,596,398 | B2 | 9/2009 | Al-Ali et al. |
| 7,618,375 | B2 | 11/2009 | Flaherty |
| D606,659 | S | 12/2009 | Kiani et al. |
| 7,647,083 | B2 | 1/2010 | Al-Ali et al. |
| D609,193 | S | 2/2010 | Al-Ali et al. |
| D614,305 | S | 4/2010 | Al-Ali et al. |
| RE41,317 | E | 5/2010 | Parker |
| 7,729,733 | B2 | 6/2010 | Al-Ali et al. |
| 7,734,320 | B2 | 6/2010 | Al-Ali |
| 7,761,127 | B2 | 7/2010 | Al-Ali et al. |
| 7,761,128 | B2 | 7/2010 | Al-Ali et al. |
| 7,764,982 | B2 | 7/2010 | Dalke et al. |
| D621,516 | S | 8/2010 | Kiani et al. |
| 7,791,155 | B2 | 9/2010 | Diab |
| 7,801,581 | B2 | 9/2010 | Diab |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,899,518 | B2 | 3/2011 | Trepagnier et al. |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,919,713 | B2 | 4/2011 | Al-Ali et al. |
| 7,937,128 | B2 | 5/2011 | Al-Ali |
| 7,937,129 | B2 | 5/2011 | Mason et al. |

(56) References Cited

U.S. PATENT DOCUMENTS

| | | | |
|---|---|---|---|
| 7,937,130 | B2 | 5/2011 | Diab et al. |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |
| 7,988,637 | B2 | 8/2011 | Diab |
| 7,990,382 | B2 | 8/2011 | Kiani |
| 7,991,446 | B2 | 8/2011 | Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,727 | B2 | 10/2011 | Schurman et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| RE43,169 | E | 2/2012 | Parker |
| 8,118,620 | B2 | 2/2012 | Al-Ali et al. |
| 8,126,528 | B2 | 2/2012 | Diab et al. |
| 8,128,572 | B2 | 3/2012 | Diab et al. |
| 8,130,105 | B2 | 3/2012 | Al-Ali et al. |
| 8,145,287 | B2 | 3/2012 | Diab et al. |
| 8,150,487 | B2 | 4/2012 | Diab et al. |
| 8,175,672 | B2 | 5/2012 | Parker |
| 8,180,420 | B2 | 5/2012 | Diab et al. |
| 8,182,443 | B1 | 5/2012 | Kiani |
| 8,185,180 | B2 | 5/2012 | Diab et al. |
| 8,190,223 | B2 | 5/2012 | Al-Ali et al. |
| 8,190,227 | B2 | 5/2012 | Diab et al. |
| 8,203,438 | B2 | 6/2012 | Kiani et al. |
| 8,203,704 | B2 | 6/2012 | Merritt et al. |
| 8,204,566 | B2 | 6/2012 | Schurman et al. |
| 8,219,172 | B2 | 7/2012 | Schurman et al. |
| 8,224,411 | B2 | 7/2012 | Al-Ali et al. |
| 8,228,181 | B2 | 7/2012 | Al-Ali |
| 8,229,533 | B2 | 7/2012 | Diab et al. |
| 8,233,955 | B2 | 7/2012 | Al-Ali et al. |
| 8,244,325 | B2 | 8/2012 | Al-Ali et al. |
| 8,255,026 | B1 | 8/2012 | Al-Ali |
| 8,255,027 | B2 | 8/2012 | Al-Ali et al. |
| 8,255,028 | B2 | 8/2012 | Al-Ali et al. |
| 8,260,577 | B2 | 9/2012 | Weber et al. |
| 8,265,723 | B1 | 9/2012 | McHale et al. |
| 8,274,360 | B2 | 9/2012 | Sampath et al. |
| 8,301,217 | B2 | 10/2012 | Al-Ali et al. |
| 8,306,596 | B2 | 11/2012 | Schurman et al. |
| 8,310,336 | B2 | 11/2012 | Muhsin et al. |
| 8,315,683 | B2 | 11/2012 | Al-Ali et al. |
| RE43,860 | E | 12/2012 | Parker |
| 8,337,403 | B2 | 12/2012 | Al-Ali et al. |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,359,080 | B2 | 1/2013 | Diab et al. |
| 8,364,223 | B2 | 1/2013 | Al-Ali et al. |
| 8,364,226 | B2 | 1/2013 | Diab et al. |
| 8,374,665 | B2 | 2/2013 | Lamego |
| 8,385,995 | B2 | 2/2013 | Al-Ali et al. |
| 8,385,996 | B2 | 2/2013 | Smith et al. |
| 8,388,353 | B2 | 3/2013 | Kiani et al. |
| 8,399,822 | B2 | 3/2013 | Al-Ali |
| 8,401,602 | B2 | 3/2013 | Kiani |
| 8,401,607 | B2 | 3/2013 | Mannheimer |
| 8,405,608 | B2 | 3/2013 | Al-Ali et al. |
| 8,414,499 | B2 | 4/2013 | Al-Ali et al. |
| 8,418,524 | B2 | 4/2013 | Al-Ali |
| 8,423,106 | B2 | 4/2013 | Lamego et al. |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,455,290 | B2 | 6/2013 | Siskavich |
| 8,457,703 | B2 | 6/2013 | Al-Ali |
| 8,457,707 | B2 | 6/2013 | Kiani |
| 8,463,349 | B2 | 6/2013 | Diab et al. |
| 8,466,286 | B2 | 6/2013 | Bellott et al. |
| 8,471,713 | B2 | 6/2013 | Poeze et al. |
| 8,473,020 | B2 | 6/2013 | Kiani et al. |
| 8,483,787 | B2 | 7/2013 | Al-Ali et al. |
| 8,489,364 | B2 | 7/2013 | Weber et al. |
| 8,498,684 | B2 | 7/2013 | Weber et al. |
| 8,504,128 | B2 | 8/2013 | Blank et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,554,297 | B2 | 10/2013 | Moon et al. |
| 8,560,032 | B2 | 10/2013 | Al-Ali et al. |
| 8,560,034 | B1 | 10/2013 | Diab et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,577,431 | B2 | 11/2013 | Lamego et al. |
| 8,581,732 | B2 | 11/2013 | Al-Ali et al. |
| 8,584,345 | B2 | 11/2013 | Al-Ali et al. |
| 8,588,880 | B2 | 11/2013 | Abdul-Hafiz et al. |
| 8,600,467 | B2 | 12/2013 | Al-Ali et al. |
| 8,606,342 | B2 | 12/2013 | Diab |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | Macneish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |
| 8,721,541 | B2 | 5/2014 | Al-Ali et al. |
| 8,721,542 | B2 | 5/2014 | Al-Ali et al. |
| 8,723,677 | B1 | 5/2014 | Kiani |
| 8,740,792 | B1 | 6/2014 | Kiani et al. |
| 8,754,776 | B2 | 6/2014 | Poeze et al. |
| 8,755,535 | B2 | 6/2014 | Telfort et al. |
| 8,755,856 | B2 | 6/2014 | Diab et al. |
| 8,755,872 | B1 | 6/2014 | Marinow |
| 8,761,850 | B2 | 6/2014 | Lamego |
| 8,764,671 | B2 | 7/2014 | Kiani |
| 8,768,423 | B2 | 7/2014 | Shakespeare et al. |
| 8,771,204 | B2 | 7/2014 | Telfort et al. |
| 8,777,634 | B2 | 7/2014 | Kiani et al. |
| 8,781,543 | B2 | 7/2014 | Diab et al. |
| 8,781,544 | B2 | 7/2014 | Al-Ali et al. |
| 8,781,549 | B2 | 7/2014 | Al-Ali et al. |
| 8,788,003 | B2 | 7/2014 | Schurman et al. |

(56) References Cited

U.S. PATENT DOCUMENTS

| | | | |
|---|---|---|---|
| 8,790,268 | B2 | 7/2014 | Al-Ali |
| 8,801,613 | B2 | 8/2014 | Al-Ali et al. |
| 8,821,397 | B2 | 9/2014 | Al-Ali et al. |
| 8,821,415 | B2 | 9/2014 | Al-Ali et al. |
| 8,830,449 | B1 | 9/2014 | Lamego et al. |
| 8,831,700 | B2 | 9/2014 | Schurman et al. |
| 8,838,196 | B2 | 9/2014 | Mannheimer |
| 8,840,549 | B2 | 9/2014 | Al-Ali et al. |
| 8,847,740 | B2 | 9/2014 | Kiani et al. |
| 8,849,365 | B2 | 9/2014 | Smith et al. |
| 8,852,094 | B2 | 10/2014 | Al-Ali et al. |
| 8,852,115 | B2 | 10/2014 | Muir |
| 8,852,994 | B2 | 10/2014 | Wojtczuk et al. |
| 8,868,147 | B2 | 10/2014 | Stippick et al. |
| 8,868,150 | B2 | 10/2014 | Al-Ali et al. |
| 8,870,792 | B2 | 10/2014 | Al-Ali et al. |
| 8,886,271 | B2 | 11/2014 | Kiani et al. |
| 8,888,539 | B2 | 11/2014 | Al-Ali et al. |
| 8,888,708 | B2 | 11/2014 | Diab et al. |
| 8,892,180 | B2 | 11/2014 | Weber et al. |
| 8,897,847 | B2 | 11/2014 | Al-Ali |
| 8,909,310 | B2 | 12/2014 | Lamego et al. |
| 8,911,377 | B2 | 12/2014 | Al-Ali |
| 8,912,909 | B2 | 12/2014 | Al-Ali et al. |
| 8,920,317 | B2 | 12/2014 | Al-Ali et al. |
| 8,921,699 | B2 | 12/2014 | Al-Ali et al. |
| 8,922,382 | B2 | 12/2014 | Al-Ali et al. |
| 8,929,964 | B2 | 1/2015 | Al-Ali et al. |
| 8,942,777 | B2 | 1/2015 | Diab et al. |
| 8,948,834 | B2 | 2/2015 | Diab et al. |
| 8,948,835 | B2 | 2/2015 | Diab |
| 8,956,294 | B2 | 2/2015 | McCombie et al. |
| 8,965,471 | B2 | 2/2015 | Lamego |
| 8,983,564 | B2 | 3/2015 | Al-Ali |
| 8,989,831 | B2 | 3/2015 | Al-Ali et al. |
| 8,996,085 | B2 | 3/2015 | Kiani et al. |
| 8,998,809 | B2 | 4/2015 | Kiani |
| 9,028,407 | B1 | 5/2015 | Bennett-Guerrero |
| 9,028,429 | B2 | 5/2015 | Telfort et al. |
| 9,037,207 | B2 | 5/2015 | Al-Ali et al. |
| 9,060,721 | B2 | 6/2015 | Reichgott et al. |
| 9,066,666 | B2 | 6/2015 | Kiani |
| 9,066,680 | B1 | 6/2015 | Al-Ali et al. |
| 9,072,474 | B2 | 7/2015 | Al-Ali et al. |
| 9,078,560 | B2 | 7/2015 | Schurman et al. |
| 9,084,569 | B2 | 7/2015 | Weber et al. |
| 9,095,316 | B2 | 8/2015 | Welch et al. |
| 9,106,038 | B2 | 8/2015 | Telfort et al. |
| 9,107,625 | B2 | 8/2015 | Telfort et al. |
| 9,107,626 | B2 | 8/2015 | Al-Ali et al. |
| 9,113,831 | B2 | 8/2015 | Al-Ali |
| 9,113,832 | B2 | 8/2015 | Al-Ali |
| 9,119,595 | B2 | 9/2015 | Lamego |
| 9,131,881 | B2 | 9/2015 | Diab et al. |
| 9,131,882 | B2 | 9/2015 | Al-Ali et al. |
| 9,131,883 | B2 | 9/2015 | Al-Ali |
| 9,131,917 | B2 | 9/2015 | Telfort et al. |
| 9,138,180 | B1 | 9/2015 | Coverston et al. |
| 9,138,182 | B2 | 9/2015 | Al-Ali et al. |
| 9,138,192 | B2 | 9/2015 | Weber et al. |
| 9,142,117 | B2 | 9/2015 | Muhsin et al. |
| 9,153,112 | B1 | 10/2015 | Kiani et al. |
| 9,153,121 | B2 | 10/2015 | Kiani et al. |
| 9,161,696 | B2 | 10/2015 | Al-Ali et al. |
| 9,161,713 | B2 | 10/2015 | Al-Ali et al. |
| 9,167,995 | B2 | 10/2015 | Lamego et al. |
| 9,176,141 | B2 | 11/2015 | Al-Ali et al. |
| 9,186,102 | B2 | 11/2015 | Bruinsma et al. |
| 9,192,312 | B2 | 11/2015 | Al-Ali |
| 9,192,329 | B2 | 11/2015 | Al-Ali |
| 9,192,351 | B1 | 11/2015 | Telfort et al. |
| 9,195,385 | B2 | 11/2015 | Al-Ali et al. |
| 9,211,072 | B2 | 12/2015 | Kiani |
| 9,211,095 | B1 | 12/2015 | Al-Ali |
| 9,218,454 | B2 | 12/2015 | Kiani et al. |
| 9,226,696 | B2 | 1/2016 | Kiani |
| 9,241,662 | B2 | 1/2016 | Al-Ali et al. |
| 9,245,668 | B1 | 1/2016 | Vo et al. |
| 9,259,185 | B2 | 2/2016 | Abdul-Hafiz et al. |
| 9,267,572 | B2 | 2/2016 | Barker et al. |
| 9,277,880 | B2 | 3/2016 | Poeze et al. |
| 9,289,167 | B2 | 3/2016 | Diab et al. |
| 9,295,421 | B2 | 3/2016 | Kiani et al. |
| 9,307,928 | B1 | 4/2016 | Al-Ali et al. |
| 9,323,894 | B2 | 4/2016 | Kiani |
| D755,392 | S | 5/2016 | Hwang et al. |
| 9,326,712 | B1 | 5/2016 | Kiani |
| 9,333,316 | B2 | 5/2016 | Kiani |
| 9,339,220 | B2 | 5/2016 | Lamego et al. |
| 9,341,565 | B2 | 5/2016 | Lamego et al. |
| 9,351,673 | B2 | 5/2016 | Diab et al. |
| 9,351,675 | B2 | 5/2016 | Al-Ali et al. |
| 9,364,181 | B2 | 6/2016 | Kiani et al. |
| 9,368,671 | B2 | 6/2016 | Wojtczuk et al. |
| 9,370,325 | B2 | 6/2016 | Al-Ali et al. |
| 9,370,326 | B2 | 6/2016 | McHale et al. |
| 9,370,335 | B2 | 6/2016 | Al-ali et al. |
| 9,375,185 | B2 | 6/2016 | Ali et al. |
| 9,386,953 | B2 | 7/2016 | Al-Ali |
| 9,386,961 | B2 | 7/2016 | Al-Ali et al. |
| 9,392,945 | B2 | 7/2016 | Al-Ali et al. |
| 9,397,448 | B2 | 7/2016 | Al-Ali et al. |
| 9,408,542 | B1 | 8/2016 | Kinast et al. |
| 9,436,645 | B2 | 9/2016 | Al-Ali et al. |
| 9,445,759 | B1 | 9/2016 | Lamego et al. |
| 9,466,919 | B2 | 10/2016 | Kiani et al. |
| 9,474,474 | B2 | 10/2016 | Lamego et al. |
| 9,480,422 | B2 | 11/2016 | Al-Ali |
| 9,480,435 | B2 | 11/2016 | Olsen |
| 9,492,110 | B2 | 11/2016 | Al-Ali et al. |
| 9,510,779 | B2 | 12/2016 | Poeze et al. |
| 9,517,024 | B2 | 12/2016 | Kiani et al. |
| 9,532,722 | B2 | 1/2017 | Lamego et al. |
| 9,538,949 | B2 | 1/2017 | Al-Ali et al. |
| 9,538,980 | B2 | 1/2017 | Telfort et al. |
| 9,549,696 | B2 | 1/2017 | Lamego et al. |
| 9,554,737 | B2 | 1/2017 | Schurman et al. |
| 9,560,996 | B2 | 2/2017 | Kiani |
| 9,560,998 | B2 | 2/2017 | Al-Ali et al. |
| 9,566,019 | B2 | 2/2017 | Al-Ali et al. |
| 9,579,039 | B2 | 2/2017 | Jansen et al. |
| 9,591,975 | B2 | 3/2017 | Dalvi et al. |
| 9,622,693 | B2 | 4/2017 | Diab |
| D788,312 | S | 5/2017 | Al-Ali et al. |
| 9,636,055 | B2 | 5/2017 | Al-Ali et al. |
| 9,636,056 | B2 | 5/2017 | Al-Ali |
| 9,649,054 | B2 | 5/2017 | Lamego et al. |
| 9,662,052 | B2 | 5/2017 | Al-Ali et al. |
| 9,668,679 | B2 | 6/2017 | Schurman et al. |
| 9,668,680 | B2 | 6/2017 | Bruinsma et al. |
| 9,668,703 | B2 | 6/2017 | Al-Ali |
| 9,675,286 | B2 | 6/2017 | Diab |
| 9,687,160 | B2 | 6/2017 | Kiani |
| 9,693,719 | B2 | 7/2017 | Al-Ali et al. |
| 9,693,737 | B2 | 7/2017 | Al-Ali |
| 9,697,928 | B2 | 7/2017 | Al-Ali et al. |
| 9,717,425 | B2 | 8/2017 | Kiani et al. |
| 9,717,458 | B2 | 8/2017 | Lamego et al. |
| 9,724,016 | B1 | 8/2017 | Al-Ali et al. |
| 9,724,024 | B2 | 8/2017 | Al-Ali |
| 9,724,025 | B1 | 8/2017 | Kiani et al. |
| 9,730,640 | B2 | 8/2017 | Diab et al. |
| 9,743,887 | B2 | 8/2017 | Al-Ali et al. |
| 9,749,232 | B2 | 8/2017 | Sampath et al. |
| 9,750,442 | B2 | 9/2017 | Olsen |
| 9,750,443 | B2 | 9/2017 | Smith et al. |
| 9,750,461 | B1 | 9/2017 | Telfort |
| 9,775,545 | B2 | 10/2017 | Al-Ali et al. |
| 9,775,546 | B2 | 10/2017 | Diab et al. |
| 9,775,570 | B2 | 10/2017 | Al-Ali |
| 9,778,079 | B1 | 10/2017 | Al-Ali et al. |
| 9,782,077 | B2 | 10/2017 | Lamego et al. |
| 9,782,110 | B2 | 10/2017 | Kiani |
| 9,787,568 | B2 | 10/2017 | Lamego et al. |

(56) References Cited

U.S. PATENT DOCUMENTS 9,788,735 B2 10/2017 Al-Ali
9,788,768 B2 10/2017 Al-Ali et al.
9,795,300 B2 10/2017 Al-Ali
9,795,310 B2 10/2017 Al-Ali
9,795,358 B2 10/2017 Telfort et al.
9,795,739 B2 10/2017 Al-Ali et al.
9,801,556 B2 10/2017 Kiani
9,801,588 B2 10/2017 Weber et al.
9,808,188 B1 11/2017 Perea et al.
9,814,418 B2 11/2017 Weber et al.
9,820,691 B2 11/2017 Kiani
9,833,152 B2 12/2017 Kiani et al.
9,833,180 B2 12/2017 Shakespeare et al.
9,839,379 B2 12/2017 Al-Ali et al.
9,839,381 B1 12/2017 Weber et al.
9,847,002 B2 12/2017 Kiani et al.
9,847,749 B2 12/2017 Kiani et al.
9,848,800 B1 12/2017 Lee et al.
9,848,806 B2 12/2017 Al-Ali et al.
9,848,807 B2 12/2017 Lamego
9,861,298 B2 1/2018 Eckerbom et al.
9,861,304 B2 1/2018 Al-Ali et al.
9,861,305 B1 1/2018 Weber et al.
9,867,578 B2 1/2018 Al-Ali et al.
9,872,623 B2 1/2018 Al-Ali
9,876,320 B2 1/2018 Coverston et al.
9,877,650 B2 1/2018 Muhsin et al.
9,877,686 B2 1/2018 Al-Ali et al.
9,891,079 B2 2/2018 Dalvi
9,895,107 B2 2/2018 Al-Ali et al.
9,913,617 B2 3/2018 Al-Ali et al.
9,924,893 B2 3/2018 Schurman et al.
9,924,897 B1 3/2018 Abdul-Hafiz
9,936,917 B2 4/2018 Poeze et al.
9,943,269 B2 4/2018 Muhsin et al.
9,949,676 B2 4/2018 Al-Ali
9,955,937 B2 5/2018 Telfort
9,965,946 B2 5/2018 Al-Ali
9,980,667 B2 5/2018 Kiani et al.
D820,865 S 6/2018 Muhsin et al.
9,986,919 B2 6/2018 Lamego et al.
9,986,952 B2 6/2018 Dalvi et al.
9,989,560 B2 6/2018 Poeze et al.
9,993,207 B2 6/2018 Al-Ali et al.
10,007,758 B2 6/2018 Al-Ali et al.
D822,215 S 7/2018 Al-Ali et al.
D822,216 S 7/2018 Barker et al.
10,010,276 B2 7/2018 Al-Ali et al.
10,032,002 B2 7/2018 Kiani et al.
10,039,482 B2 8/2018 Al-Ali et al.
10,052,037 B2 8/2018 Kinast et al.
10,058,275 B2 8/2018 Al-Ali et al.
10,064,562 B2 9/2018 Al-Ali
10,086,138 B1 10/2018 Novak, Jr.
10,092,200 B2 10/2018 Al-Ali et al.
10,092,249 B2 10/2018 Kiani et al.
10,098,550 B2 10/2018 Al-Ali et al.
10,098,591 B2 10/2018 Al-Ali et al.
10,098,610 B2 10/2018 Al-Ali et al.
D833,624 S 11/2018 DeJong et al.
10,123,726 B2 11/2018 Al-Ali et al.
10,130,289 B2 11/2018 Al-Ali et al.
10,130,291 B2 11/2018 Schurman et al.
D835,282 S 12/2018 Barker et al.
D835,283 S 12/2018 Barker et al.
D835,284 S 12/2018 Barker et al.
D835,285 S 12/2018 Barker et al.
10,149,616 B2 12/2018 Al-Ali et al.
10,154,815 B2 12/2018 Al-Ali et al.
10,159,412 B2 12/2018 Lamego et al.
10,188,296 B2 1/2019 Al-Ali et al.
10,188,331 B1 1/2019 Al-Ali et al.
10,188,348 B2 1/2019 Kiani et al.
RE47,218 E 2/2019 Ali-Ali
RE47,244 E 2/2019 Kiani et al.
RE47,249 E 2/2019 Kiani et al.
10,194,847 B2 2/2019 Al-Ali
10,194,848 B1 2/2019 Kiani et al.
10,201,298 B2 2/2019 Al-Ali et al.
10,205,272 B2 2/2019 Kiani et al.
10,205,291 B2 2/2019 Scruggs et al.
10,213,108 B2 2/2019 Al-Ali
10,219,706 B2 3/2019 Al-Ali
10,219,746 B2 3/2019 McHale et al.
10,226,187 B2 3/2019 Al-Ali et al.
10,226,576 B2 3/2019 Kiani
10,231,657 B2 3/2019 Al-Ali et al.
10,231,670 B2 3/2019 Blank et al.
10,231,676 B2 3/2019 Al-Ali et al.
RE47,353 E 4/2019 Kiani et al.
10,251,585 B2 4/2019 Al-Ali et al.
10,251,586 B2 4/2019 Lamego
10,255,994 B2 4/2019 Sampath et al.
10,258,265 B1 4/2019 Poeze et al.
10,258,266 B1 4/2019 Poeze et al.
10,271,748 B2 4/2019 Al-Ali
10,278,626 B2 5/2019 Schurman et al.
10,278,648 B2 5/2019 Al-Ali et al.
10,279,247 B2 5/2019 Kiani
10,292,628 B1 5/2019 Poeze et al.
10,292,657 B2 5/2019 Abdul-Hafiz et al.
10,292,664 B2 5/2019 Al-Ali
10,299,708 B1 5/2019 Poeze et al.
10,299,709 B2 5/2019 Perea et al.
10,305,775 B2 5/2019 Lamego et al.
10,307,111 B2 6/2019 Muhsin et al.
10,325,681 B2 6/2019 Sampath et al.
10,327,337 B2 6/2019 Triman et al.
10,327,713 B2 6/2019 Barker et al.
10,332,630 B2 6/2019 Al-Ali
10,335,033 B2 7/2019 Al-Ali
10,335,068 B2 7/2019 Poeze et al.
10,335,072 B2 7/2019 Al-Ali et al.
10,342,470 B2 7/2019 Al-Ali et al.
10,342,487 B2 7/2019 Al-Ali et al.
10,342,497 B2 7/2019 Al-Ali et al.
10,349,895 B2 7/2019 Telfort et al.
10,349,898 B2 7/2019 Al-Ali et al.
10,354,504 B2 7/2019 Kiani et al.
10,357,206 B2 7/2019 Weber et al.
10,357,209 B2 7/2019 Al-Ali
10,366,787 B2 7/2019 Sampath et al.
10,368,787 B2 8/2019 Reichgott et al.
10,376,190 B1 8/2019 Poeze et al.
10,376,191 B1 8/2019 Poeze et al.
10,383,520 B2 8/2019 Wojtczuk et al.
10,383,527 B2 8/2019 Al-Ali
10,388,120 B2 8/2019 Muhsin et al.
10,398,320 B2 9/2019 Kiani et al.
10,405,804 B2 9/2019 Al-Ali
10,413,666 B2 9/2019 Al-Ali et al.
10,420,493 B2 9/2019 Al-Ali et al.
10,433,776 B2 10/2019 Al-Ali
10,441,181 B1 10/2019 Telfort et al.
2004/0162499 A1 8/2004 Nagai et al.
2005/0027182 A1 2/2005 Siddiqui
2005/0177096 A1 8/2005 Bollish
2005/0240091 A1 10/2005 Lynn
2006/0220881 A1 10/2006 Al-Ali
2007/0156031 A1* 7/2007 Sullivan ..... A61B 5/7282 600/300
2007/0282478 A1 12/2007 Al-Ali et al.
2008/0103375 A1 5/2008 Kiani
2008/0157980 A1 7/2008 Sachanandani et al.
2008/0255438 A1 10/2008 Saidara
2008/0281168 A1 11/2008 Gibson
2009/0040874 A1 2/2009 Rooney
2009/0210163 A1 8/2009 Ochs et al.
2009/0247848 A1* 10/2009 Baker, Jr. ..... A61B 5/14551 600/323
2009/0247849 A1 10/2009 McCutcheon et al.
2009/0247924 A1 10/2009 Lamego et al.
2009/0247984 A1 10/2009 Lamego et al.
2009/0275813 A1 11/2009 Davis

(56) References Cited

U.S. PATENT DOCUMENTS

2009/0275844 A1 11/2009 Al-Ali
2009/0299157 A1 12/2009 Telfort et al.
2010/0004518 A1 1/2010 Vo et al.
2010/0030040 A1 2/2010 Poeze et al.
2010/0113904 A1 5/2010 Batchelder et al.
2010/0261979 A1 10/2010 Kiani
2011/0001605 A1 1/2011 Kiani et al.
2011/0082711 A1 4/2011 Poeze et al.
2011/0105854 A1 5/2011 Kiani et al.
2011/0125060 A1 5/2011 Telfort et al.
2011/0208015 A1 8/2011 Welch et al.
2011/0209915 A1 9/2011 Telfort et al.
2011/0213212 A1 9/2011 Al-Ali
2011/0230733 A1 9/2011 Al-Ali
2011/0237911 A1 9/2011 Lamego et al.
2011/0237969 A1 9/2011 Eckerbom et al.
2011/0288383 A1 11/2011 Diab
2012/0041316 A1 2/2012 Al Ali et al.
2012/0046557 A1 2/2012 Kiani
2012/0059267 A1 3/2012 Lamego et al.
2012/0088984 A1 4/2012 Al-Ali et al.
2012/0116175 A1 5/2012 Al-Ali et al.
2012/0165629 A1 6/2012 Merritt et al.
2012/0179006 A1 7/2012 Jansen et al.
2012/0209082 A1 8/2012 Al-Ali
2012/0209084 A1 8/2012 Olsen et al.
2012/0227739 A1 9/2012 Kiani
2012/0232366 A1 9/2012 Kiani
2012/0265039 A1 10/2012 Kiani
2012/0283524 A1 11/2012 Kiani et al.
2012/0286955 A1 11/2012 Welch et al.
2012/0296178 A1 11/2012 Lamego et al.
2012/0319816 A1 12/2012 Al-Ali
2012/0330112 A1 12/2012 Lamego et al.
2013/0023775 A1 1/2013 Lamego et al.
2013/0041591 A1 2/2013 Lamego
2013/0045685 A1 2/2013 Kiani
2013/0046204 A1 2/2013 Lamego et al.
2013/0060108 A1 3/2013 Schurman et al.
2013/0060147 A1 3/2013 Welch et al.
2013/0096405 A1 4/2013 Garfio
2013/0096936 A1 4/2013 Sampath et al.
2013/0109935 A1 5/2013 Al-Ali et al.
2013/0162433 A1 6/2013 Muhsin et al.
2013/0190581 A1 7/2013 Al-Ali et al.
2013/0197328 A1 8/2013 Diab et al.
2013/0211214 A1 8/2013 Olsen
2013/0243021 A1 9/2013 Siskavich
2013/0253334 A1 9/2013 Al-Ali et al.
2013/0267804 A1 10/2013 Al-Ali
2013/0274571 A1 10/2013 Diab et al.
2013/0274572 A1 10/2013 Al-Ali et al.
2013/0296672 A1 11/2013 O'Neil et al.
2013/0296713 A1 11/2013 Al-Ali et al.
2013/0317370 A1 11/2013 Dalvi et al.
2013/0324808 A1 12/2013 Al-Ali et al.
2013/0331660 A1 12/2013 Al-Ali et al.
2013/0331670 A1 12/2013 Kiani
2013/0338461 A1 12/2013 Lamego et al.
2014/0012100 A1 1/2014 Al-Ali et al.
2014/0025306 A1 1/2014 Weber et al.
2014/0034353 A1 2/2014 Al-Ali et al.
2014/0051952 A1 2/2014 Reichgott et al.
2014/0051953 A1 2/2014 Lamego et al.
2014/0051954 A1 2/2014 Al-Ali et al.
2014/0058230 A1 2/2014 Abdul-Hafiz et al.
2014/0066783 A1 3/2014 Kiani et al.
2014/0077956 A1 3/2014 Sampath et al.
2014/0081100 A1 3/2014 Muhsin et al.
2014/0081175 A1 3/2014 Telfort
2014/0094667 A1 4/2014 Schurman et al.
2014/0100434 A1 4/2014 Diab et al.
2014/0114199 A1 4/2014 Lamego et al.
2014/0120564 A1 5/2014 Workman et al.
2014/0121482 A1 5/2014 Merritt et al.
2014/0121483 A1 5/2014 Kiani
2014/0125495 A1 5/2014 Al-Ali
2014/0127137 A1 5/2014 Bellott et al.
2014/0128696 A1 5/2014 Al-Ali
2014/0128699 A1 5/2014 Al-Ali et al.
2014/0129702 A1 5/2014 Lamego et al.
2014/0135588 A1 5/2014 Al-Ali et al.
2014/0142401 A1 5/2014 Al-Ali et al.
2014/0142402 A1 5/2014 Al-Ali et al.
2014/0163344 A1 6/2014 Al-Ali
2014/0163402 A1 6/2014 Lamego et al.
2014/0166076 A1 6/2014 Kiani et al.
2014/0171763 A1 6/2014 Diab
2014/0180038 A1 6/2014 Kiani
2014/0180154 A1 6/2014 Sierra et al.
2014/0187973 A1 7/2014 Brown et al.
2014/0194709 A1 7/2014 Al-Ali et al.
2014/0194711 A1 7/2014 Al-Ali
2014/0194766 A1 7/2014 Al-Ali et al.
2014/0200420 A1 7/2014 Al-Ali
2014/0200422 A1 7/2014 Weber et al.
2014/0206963 A1 7/2014 Al-Ali
2014/0213864 A1 7/2014 Abdul-Hafiz et al.
2014/0243627 A1 8/2014 Diab et al.
2014/0266790 A1 9/2014 Al-Ali et al.
2014/0275808 A1 9/2014 Poeze et al.
2014/0275835 A1 9/2014 Lamego et al.
2014/0275871 A1 9/2014 Lamego et al.
2014/0275872 A1 9/2014 Merritt et al.
2014/0275881 A1 9/2014 Lamego et al.
2014/0276115 A1 9/2014 Dalvi et al.
2014/0288400 A1 9/2014 Diab et al.
2014/0296664 A1 10/2014 Bruinsma et al.
2014/0303520 A1 10/2014 Telfort et al.
2014/0309506 A1 10/2014 Lamego et al.
2014/0309507 A1 10/2014 Baker, Jr.
2014/0309559 A1 10/2014 Telfort et al.
2014/0316228 A1 10/2014 Blank et al.
2014/0323825 A1 10/2014 Al-Ali et al.
2014/0323897 A1 10/2014 Brown et al.
2014/0323898 A1 10/2014 Purdon et al.
2014/0330092 A1 11/2014 Al-Ali et al.
2014/0330098 A1 11/2014 Merritt et al.
2014/0330099 A1 11/2014 Al-Ali et al.
2014/0333440 A1 11/2014 Kiani
2014/0336481 A1 11/2014 Shakespeare et al.
2014/0343436 A1 11/2014 Kiani
2015/0005600 A1 1/2015 Blank et al.
2015/0011907 A1 1/2015 Purdon et al.
2015/0012231 A1 1/2015 Poeze et al.
2015/0018650 A1 1/2015 Al-Ali et al.
2015/0025406 A1 1/2015 Al-Ali
2015/0032029 A1 1/2015 Al-Ali et al.
2015/0038859 A1 2/2015 Dalvi et al.
2015/0045637 A1 2/2015 Dalvi
2015/0051462 A1 2/2015 Olsen
2015/0080754 A1 3/2015 Purdon et al.
2015/0087936 A1 3/2015 Al-Ali et al.
2015/0094546 A1 4/2015 Al-Ali
2015/0097701 A1 4/2015 Al-Ali et al.
2015/0099950 A1 4/2015 Al-Ali et al.
2015/0099951 A1 4/2015 Al-Ali et al.
2015/0099955 A1 4/2015 Al-Ali et al.
2015/0101844 A1 4/2015 Al-Ali et al.
2015/0106121 A1 4/2015 Muhsin et al.
2015/0112151 A1 4/2015 Muhsin et al.
2015/0116076 A1 4/2015 Al-Ali et al.
2015/0126830 A1 5/2015 Schurman et al.
2015/0133755 A1 5/2015 Smith et al.
2015/0141781 A1 5/2015 Weber et al.
2015/0165312 A1 6/2015 Kiani
2015/0196237 A1 7/2015 Lamego
2015/0216459 A1 8/2015 Al-Ali et al.
2015/0230755 A1 8/2015 Al-Ali et al.
2015/0238722 A1 8/2015 Al-Ali
2015/0245773 A1 9/2015 Lamego et al.
2015/0245794 A1 9/2015 Al-Ali
2015/0257689 A1 9/2015 Al-Ali et al.
2015/0272514 A1 10/2015 Kiani et al.

(56) References Cited

U.S. PATENT DOCUMENTS

| | | | |
|---|---|---|---|
| 2015/0351697 | A1 | 12/2015 | Weber et al. |
| 2015/0351704 | A1 | 12/2015 | Kiani et al. |
| 2015/0359429 | A1 | 12/2015 | Al-Ali et al. |
| 2015/0366472 | A1 | 12/2015 | Kiani |
| 2015/0366507 | A1 | 12/2015 | Blank |
| 2015/0374298 | A1 | 12/2015 | Al-Ali et al. |
| 2015/0380875 | A1 | 12/2015 | Coverston et al. |
| 2016/0000362 | A1 | 1/2016 | Diab et al. |
| 2016/0007930 | A1 | 1/2016 | Weber et al. |
| 2016/0029932 | A1 | 2/2016 | Al-Ali |
| 2016/0045118 | A1 | 2/2016 | Kiani |
| 2016/0051205 | A1 | 2/2016 | Al-Ali et al. |
| 2016/0058338 | A1 | 3/2016 | Schurman et al. |
| 2016/0058347 | A1 | 3/2016 | Reichgott et al. |
| 2016/0066823 | A1 | 3/2016 | Al-Ali et al. |
| 2016/0066824 | A1 | 3/2016 | Al-Ali et al. |
| 2016/0066879 | A1 | 3/2016 | Telfort et al. |
| 2016/0072429 | A1 | 3/2016 | Kiani et al. |
| 2016/0081552 | A1 | 3/2016 | Wojtczuk et al. |
| 2016/0095543 | A1 | 4/2016 | Telfort et al. |
| 2016/0095548 | A1 | 4/2016 | Al-Ali et al. |
| 2016/0103598 | A1 | 4/2016 | Al-Ali et al. |
| 2016/0113527 | A1 | 4/2016 | Al-Ali et al. |
| 2016/0143548 | A1 | 5/2016 | Al-Ali |
| 2016/0166182 | A1 | 6/2016 | Al-Ali et al. |
| 2016/0166183 | A1 | 6/2016 | Poeze et al. |
| 2016/0166188 | A1 | 6/2016 | Bruinsma et al. |
| 2016/0166210 | A1 | 6/2016 | Al-Ali |
| 2016/0192869 | A1 | 7/2016 | Kiani et al. |
| 2016/0196388 | A1 | 7/2016 | Lamego |
| 2016/0197436 | A1 | 7/2016 | Barker et al. |
| 2016/0213281 | A1 | 7/2016 | Eckerbom et al. |
| 2016/0228043 | A1 | 8/2016 | O'Neil et al. |
| 2016/0233632 | A1 | 8/2016 | Scruggs et al. |
| 2016/0234944 | A1 | 8/2016 | Schmidt et al. |
| 2016/0270735 | A1 | 9/2016 | Diab et al. |
| 2016/0283665 | A1 | 9/2016 | Sampath et al. |
| 2016/0287090 | A1 | 10/2016 | Al-Ali et al. |
| 2016/0287786 | A1 | 10/2016 | Kiani |
| 2016/0296169 | A1 | 10/2016 | McHale et al. |
| 2016/0310052 | A1 | 10/2016 | Al-Ali et al. |
| 2016/0314260 | A1 | 10/2016 | Kiani |
| 2016/0324486 | A1 | 11/2016 | Al-Ali et al. |
| 2016/0324488 | A1 | 11/2016 | Olsen |
| 2016/0327984 | A1 | 11/2016 | Al-Ali et al. |
| 2016/0328528 | A1 | 11/2016 | Al-Ali et al. |
| 2016/0331332 | A1 | 11/2016 | Al-Ali |
| 2016/0367173 | A1 | 12/2016 | Dalvi et al. |
| 2017/0007134 | A1 | 1/2017 | Al-Ali et al. |
| 2017/0007190 | A1 | 1/2017 | Al-Ali et al. |
| 2017/0007198 | A1 | 1/2017 | Al-Ali et al. |
| 2017/0014083 | A1 | 1/2017 | Diab et al. |
| 2017/0014084 | A1 | 1/2017 | Al-Ali et al. |
| 2017/0021099 | A1 | 1/2017 | Al-Ali et al. |
| 2017/0024748 | A1 | 1/2017 | Haider |
| 2017/0027456 | A1 | 2/2017 | Kinast et al. |
| 2017/0042488 | A1 | 2/2017 | Muhsin |
| 2017/0055847 | A1 | 3/2017 | Kiani et al. |
| 2017/0055851 | A1 | 3/2017 | Al-Ali |
| 2017/0055882 | A1 | 3/2017 | Al-Ali et al. |
| 2017/0055887 | A1 | 3/2017 | Al-Ali |
| 2017/0055896 | A1 | 3/2017 | Al-Ali et al. |
| 2017/0079594 | A1 | 3/2017 | Telfort et al. |
| 2017/0086723 | A1 | 3/2017 | Al-Ali et al. |
| 2017/0143281 | A1 | 5/2017 | Olsen |
| 2017/0147774 | A1 | 5/2017 | Kiani |
| 2017/0156620 | A1 | 6/2017 | Al-Ali et al. |
| 2017/0173632 | A1 | 6/2017 | Al-Ali |
| 2017/0187146 | A1 | 6/2017 | Kiani et al. |
| 2017/0188919 | A1 | 7/2017 | Al-Ali et al. |
| 2017/0196464 | A1 | 7/2017 | Jansen et al. |
| 2017/0196470 | A1 | 7/2017 | Lamego et al. |
| 2017/0202490 | A1 | 7/2017 | Al-Ali et al. |
| 2017/0224231 | A1 | 8/2017 | Al-Ali |
| 2017/0224262 | A1 | 8/2017 | Al-Ali |
| 2017/0228516 | A1 | 8/2017 | Sampath et al. |
| 2017/0245790 | A1 | 8/2017 | Al-Ali et al. |
| 2017/0251974 | A1 | 9/2017 | Shreim et al. |
| 2017/0251975 | A1 | 9/2017 | Shreim et al. |
| 2017/0258403 | A1 | 9/2017 | Abdul-Hafiz et al. |
| 2017/0311891 | A1 | 11/2017 | Kiani et al. |
| 2017/0325728 | A1 | 11/2017 | Al-Ali et al. |
| 2017/0332976 | A1 | 11/2017 | Al-Ali et al. |
| 2017/0340293 | A1 | 11/2017 | Al-Ali et al. |
| 2017/0360310 | A1 | 12/2017 | Kiani et al. |
| 2017/0367632 | A1 | 12/2017 | Al-Ali et al. |
| 2018/0008146 | A1 | 1/2018 | Al-Ali et al. |
| 2018/0013562 | A1 | 1/2018 | Haider et al. |
| 2018/0014752 | A1 | 1/2018 | Al-Ali et al. |
| 2018/0028124 | A1 | 2/2018 | Al-Ali et al. |
| 2018/0055390 | A1 | 3/2018 | Kiani et al. |
| 2018/0055430 | A1 | 3/2018 | Diab et al. |
| 2018/0064381 | A1 | 3/2018 | Shakespeare et al. |
| 2018/0070867 | A1 | 3/2018 | Smith et al. |
| 2018/0082767 | A1 | 3/2018 | Al-Ali et al. |
| 2018/0085068 | A1 | 3/2018 | Telfort |
| 2018/0087937 | A1 | 3/2018 | Al-Ali et al. |
| 2018/0103874 | A1 | 4/2018 | Lee et al. |
| 2018/0103905 | A1 | 4/2018 | Kiani |
| 2018/0125368 | A1 | 5/2018 | Lamego et al. |
| 2018/0125430 | A1 | 5/2018 | Al-Ali et al. |
| 2018/0125445 | A1 | 5/2018 | Telfort et al. |
| 2018/0132769 | A1 | 5/2018 | Weber et al. |
| 2018/0146901 | A1 | 5/2018 | Al-Ali et al. |
| 2018/0146902 | A1 | 5/2018 | Kiani et al. |
| 2018/0153442 | A1 | 6/2018 | Eckerbom et al. |
| 2018/0153446 | A1 | 6/2018 | Kiani |
| 2018/0153447 | A1 | 6/2018 | Al-Ali et al. |
| 2018/0153448 | A1 | 6/2018 | Weber et al. |
| 2018/0168491 | A1 | 6/2018 | Al-Ali et al. |
| 2018/0184917 | A1 | 7/2018 | Kiani |
| 2018/0192924 | A1 | 7/2018 | Al-Ali |
| 2018/0192953 | A1 | 7/2018 | Shreim et al. |
| 2018/0199871 | A1 | 7/2018 | Pauley et al. |
| 2018/0206795 | A1 | 7/2018 | Al-Ali |
| 2018/0206815 | A1 | 7/2018 | Telfort |
| 2018/0213583 | A1 | 7/2018 | Al-Ali |
| 2018/0214090 | A1 | 8/2018 | Al-Ali et al. |
| 2018/0218792 | A1 | 8/2018 | Muhsin et al. |
| 2018/0225960 | A1 | 8/2018 | Al-Ali et al. |
| 2018/0238718 | A1 | 8/2018 | Dalvi |
| 2018/0242853 | A1 | 8/2018 | Al-Ali |
| 2018/0242921 | A1 | 8/2018 | Muhsin et al. |
| 2018/0242923 | A1 | 8/2018 | Al-Ali et al. |
| 2018/0242926 | A1 | 8/2018 | Muhsin et al. |
| 2018/0247353 | A1 | 8/2018 | Al-Ali et al. |
| 2018/0247712 | A1 | 8/2018 | Muhsin et al. |
| 2018/0256087 | A1 | 9/2018 | Al-Ali et al. |
| 2018/0285094 | A1 | 10/2018 | Housel et al. |
| 2018/0289325 | A1 | 10/2018 | Poeze et al. |
| 2018/0296161 | A1 | 10/2018 | Shreim et al. |
| 2018/0300919 | A1 | 10/2018 | Muhsin et al. |
| 2018/0310822 | A1 | 11/2018 | Indorf et al. |
| 2018/0310823 | A1 | 11/2018 | Al-Ali et al. |
| 2018/0317826 | A1 | 11/2018 | Muhsin |
| 2018/0317841 | A1 | 11/2018 | Novak, Jr. |
| 2018/0333055 | A1 | 11/2018 | Lamego et al. |
| 2018/0333087 | A1 | 11/2018 | Al-Ali |
| 2019/0000317 | A1 | 1/2019 | Muhsin et al. |
| 2019/0000362 | A1 | 1/2019 | Kiani et al. |
| 2019/0015023 | A1 | 1/2019 | Monfre |
| 2019/0029574 | A1 | 1/2019 | Schurman et al. |
| 2019/0029578 | A1 | 1/2019 | Al-Ali et al. |
| 2019/0058280 | A1 | 2/2019 | Al-Ali et al. |
| 2019/0058281 | A1 | 2/2019 | Al-Ali et al. |
| 2019/0069813 | A1 | 3/2019 | Al-Ali |
| 2019/0069814 | A1 | 3/2019 | Al-Ali |
| 2019/0076028 | A1 | 3/2019 | Al-Ali et al. |
| 2019/0082979 | A1 | 3/2019 | Al-Ali et al. |
| 2019/0090760 | A1 | 3/2019 | Kinast et al. |
| 2019/0090764 | A1 | 3/2019 | Al-Ali |
| 2019/0117070 | A1 | 4/2019 | Muhsin et al. |
| 2019/0117139 | A1 | 4/2019 | Al-Ali et al. |
| 2019/0117140 | A1 | 4/2019 | Al-Ali et al. |

(56) References Cited

U.S. PATENT DOCUMENTS

| | | | | |
|---|---|---|---|---|
| 2019/0117141 | A1 | 4/2019 | Al-Ali | |
| 2019/0117930 | A1 | 4/2019 | Al-Ali | |
| 2019/0122763 | A1 | 4/2019 | Sampath et al. | |
| 2019/0133525 | A1 | 5/2019 | Al-Ali et al. | |
| 2019/0142283 | A1 | 5/2019 | Lamego et al. | |
| 2019/0142344 | A1 | 5/2019 | Telfort et al. | |
| 2019/0150856 | A1 | 5/2019 | Kiani et al. | |
| 2019/0167161 | A1 | 6/2019 | Al-Ali et al. | |
| 2019/0175019 | A1 | 6/2019 | Al-Ali et al. | |
| 2019/0192076 | A1 | 6/2019 | McHale et al. | |
| 2019/0200941 | A1 | 7/2019 | Chandran et al. | |
| 2019/0201623 | A1 | 7/2019 | Kiani | |
| 2019/0209025 | A1 | 7/2019 | Al-Ali | |
| 2019/0214778 | A1 | 7/2019 | Scruggs et al. | |
| 2019/0216319 | A1 | 7/2019 | Poeze et al. | |
| 2019/0216370 | A1* | 7/2019 | Schurman ..... | A61B 5/0066 |
| 2019/0216379 | A1 | 7/2019 | Al-Ali et al. | |
| 2019/0221966 | A1 | 7/2019 | Kiani et al. | |
| 2019/0223804 | A1 | 7/2019 | Blank et al. | |
| 2019/0231199 | A1 | 8/2019 | Al-Ali et al. | |
| 2019/0231241 | A1 | 8/2019 | Al-Ali et al. | |
| 2019/0231270 | A1 | 8/2019 | Abdul-Hafiz et al. | |
| 2019/0239787 | A1 | 8/2019 | Pauley et al. | |
| 2019/0239824 | A1 | 8/2019 | Muhsin et al. | |
| 2019/0254578 | A1 | 8/2019 | Lamego | |
| 2019/0261857 | A1 | 8/2019 | Al-Ali | |
| 2019/0269370 | A1 | 9/2019 | Al-Ali et al. | |
| 2019/0274606 | A1 | 9/2019 | Kiani et al. | |
| 2019/0274627 | A1 | 9/2019 | Al-Ali et al. | |
| 2019/0274635 | A1 | 9/2019 | Al-Ali et al. | |
| 2019/0290136 | A1 | 9/2019 | Dalvi et al. | |
| 2019/0298270 | A1 | 10/2019 | Al-Ali et al. | |
| 2019/0304601 | A1 | 10/2019 | Sampath et al. | |
| 2019/0304605 | A1 | 10/2019 | Al-Ali | |
| 2019/0307377 | A1 | 10/2019 | Perea et al. | |
| 2019/0320906 | A1 | 10/2019 | Olsen | |
| 2019/0320959 | A1 | 10/2019 | Al-Ali | |
| 2019/0320988 | A1 | 10/2019 | Ahmed et al. | |
| 2019/0325722 | A1 | 10/2019 | Kiani et al. | |

FOREIGN PATENT DOCUMENTS

| | | |
|---|---|---|
| WO | WO 2005/087097 | 9/2005 |
| WO | WO 2009/093159 | 7/2009 |
| WO | WO 2010/014743 | 2/2010 |

OTHER PUBLICATIONS

Oct. 24, 2019 Defendant Sotera Wireless, Inc.'s First Amended Answer to Plaintiff's Complaint for Patent Infringement and Demand for Jury Trial, *Masimo Corporation* v. *Sotera Wireless and Hon Hai Precision Industry Co., Ltd.*, Case No. 3:19-cv-01100-BAS-NLS, 32 pages.

Ferrell, "Design and Construct Miniaturized Biosensor/Transmitter System," Dept. of Physics, University of Tennessee, Jun. 1999, 77 pages.

Perng et al., "Acceleration Sensing Glove (ASG)," Berkeley Sensor & Actuator Center, University of California, Berkeley, Feb. 1999, 3 pages.

Raghunath et al., "User Interfaces for Applications on a Wrist Watch, Wearable Computing Platforms," IBM TJ Watson Research Center, New York, US, Personal Ubiquitous Computing, vol. 6, issue 1, Feb. 2002, pp. 17-30.

Stein et al., "Development of a Commercially Successful Wearable Data Collection System," Digest of Papers. Second International Symposium on Wearable Computers, Pittsburgh, PA, USA, Oct. 19-20, 1998, pp. 18-24.

Billinghurst et al., "Wearable Devices: New Ways to Manage Information," Computer, vol. 32, No. 1, Jan. 1999, pp. 57-64.

Berggren, "Wireless communication in telemedicine using Bluetooth and IEEE 802.11b," Department of Information Technology, Uppsala University, Sweden, Nov. 2001, 32 pages.

Adler, "A Cost-Effective Portable Telemedicine Kit for Use in Developing Countries," Massachusetts Institute of Technology, May 2000, 96 pages.

Satava, et al., "The Physiologic Cipher at Altitude: Telemedicine and Real-Time Monitoring of Climbers on Mount Everest," Telemedicine Journal and e-Health, vol. 6, No. 3, Feb. 2000, pp. 303-313.

Fricke et al., "Wireless Sensor Review," Arthur D. Little, Inc., Cambridge, MA, Mar. 2001, 59 pages.

Haglund, "Bluetooth Software and Hardware Development," Imperial College of Science, Technology and Medicine, University of London, Sep. 2001, 66 pages.

Bilstrup et al., "Bluetooth in Industrial Environment," IEEE International Workshop on Factory Communication Systems, Feb. 2000, 9 pages.

Shoemake, "Wi-Fi (IEEE 802.11b) and Bluetooth: Coexistence Issues and Solutions for the 2.4 GHz ISM Band," Texas Instruments, Feb. 2001, 18 pages.

Aljuaied, "Bluetooth Technology and Its Implementation in Sensing Devices," Research Office Naval Postgraduate School, Monterey, CA, Sep. 2001, 75 pages.

Seruca et al., "Enterprise Information Systems VI," Springer, Kluwer Academic Publishers, Mar. 2006, 334 pages.

Tsien, "TrendFinder: Automated Detection of Alarmable Trends," Massachusetts Institute of Technology, Apr. 2000, 240 pages.

Tsien, "Reducing False Alarms in the Intensive Care Unit: A Systematic Comparison of Four Algorithms," Proceedings of the AMIA Annual Fall Symposium, 1997, p. 894.

Myerson et al., "An Evaluation of Ventilator Monitoring Alarms," Anaesthesia and Intensive Care, vol. 14, No. 2, May 1986, pp. 174-185.

Huang, "Intelligent Alarms: Allocating Attention Among Concurrent Processes," Stanford University, Mar. 1999, 198 pages.

Mora et al., "Intelligent Patient Monitoring and Management Systems: A Review," IEEE Engineering in Medicine and Biology Magazine, vol. 12, issue 4, Decmber 1993, pp. 23-33.

Zhang et al., "Prospective Trials of Intelligent Alarm Algorithms for Patient Monitoring," Proceedings of the AMIA Symposium, 2001, p. 1068.

Malangi, "Simulation and mathematical notation of alarms unit for computer assisted resuscitation algorithm," New Jersey Institute or Technology, Digital Commons @ NJIT, These 526, Fall 2003.

Schoenberg MD et al., "Making ICU Alarms Meaningful: A Comparison of Traditional vs. Trend-Based Algorithms," Proceedings. AMIA Symposium, 1999, pp. 379-383.

Jones, "Autonomous Patient Monitoring with a Pressure Sensor Array," Carleton University, Ontario, Canada, Sep. 2006, 185 pages.

Taenzer et al., "Impact of Pulse Oximetry Surveillance on Rescue Events and Intensive Care Unit Transfers: A Before-and-After Concurrence Study," Anesthesiology—The Journal of the American Society of Anesthesiologists, Inc., vol. 112, No. 2, Feb. 2010, pp. 282-287.

International Search Report for PCT/US2009/052146, dated Dec. 15, 2009.

International Preliminary Report on Patentability and Written Opinion for PCT/US2009/052146 dated Feb. 10, 2011.

Rheineck-Leyssius, MD, et al., "Advanced Pulse Oximeter Signal Processing Technology Compared to Simple Averaging. I. Effect on Frequency of Alarms in the Operating Room", Journal of Clinical Anesthesia, The Netherlands, May 1999, vol. 11, pp. 192-195.

Cust, AE, et al., "Alarm settings for the Marquette 8000 pulse oximeter to prevent hyperoxic and hypoxic episodes", Journal Paediatric Child Health, 1999, vol. 35, pp. 159-162.

Lawless, Stephen T., "Crying wolf: False alarms in a pediatric intensive care unit", Critical Care Medicine, 1994, vol. 22, No. 6, pp. 981-985.

Informal Expert Report of Dr. Stephen Barker, Lead Case No. 16-05968-LT11, executed Feb. 10, 2017.

Impact of Clinical Alarms on Patient Safety, ACCE Healthcare Technology Foundation, 2006, 20 pages.

(56) References Cited

OTHER PUBLICATIONS

Taenzer, M.D., Andreas, "Impact of Pulse Oximetry Surveillance on Rescue Events and Intensive Care Unit Transfers", The American Society of Anesthesiologists, Inc., Feb. 2010, vol. 112, No. 2, pp. 282-287.
Stefanescu, MD MSc, Beatrice, "Improved Filtering of Pulse Oximeter Monitoring Alarms in the Neonatal ICU: Bedside Significance", Respiratory Care, Jan. 2016, vol. 61, No. 1, pp. 85-89.
Rheineck-Leyssius, A.T., et al., "Influence of pulse oximeter lower alarm limit on the incidence of hypoxaemia in the recovery room", British Journal of Anaesthesia, 1997, vol. 79, pp. 460-464.
Rheineck-Leyssius, MD, Aart, et al., "Influence of Pulse Oximeter Settings on the Frequency of Alarms, and Detection of Hypoxemia", Journal of Clinical Monitoring and Computing, 1998, vol. 14, pp. 151-156.
Pan, MD., Peter, "Intraoperative Pulse Oximetry: Frequency and Distribution of Discrepant Data", Journal of Clinical Monitoring and Computing, Nov./Dec. 1994, vol. 6, pp. 491-495.
Graham, Kelly, et al., Monitor Alarm Fatigue: Standardizing Use of Physiological Monitors and Decreasing Nuisance Alarms, American Journal of Critical Care, Jan. 2010, vol. 19, No. 1, pp. 27-37.
Barker, PhD, MD, Steven, "'Motion-Resistant' Pulse Oximetry: A Comparison of New and Old Models" Department of Anesthesiology, 2002, vol. 95, pp. 967-972.
National Patient Safety Goals Effective Jan. 1, 2015, Hospital Accreditation Program, The Joint Commission, Jan. 2015, pp. 1-17.
Brostowicz, Heather, et al. Oxygen saturation monitoring in the Neonatal Intensive Care Unit (NICU): Evaluation of a new alarm management, Journal of Neonatal-Perinatal Medicine 3, 2010, pp. 135-139.
Kowalczyk, Liz, "Patient alarms often unheard, unheeded" The Boston Globe, Feb. 13, 2011, in 5 pages.
Taenzer, Andreas, et al., "Postoperative Monitoring—The Dartmouth Experience", The Official Journal of the Anesthesia Patient Safety Foundation, Spring-Summer 2012, vol. 27, No. 1, pp. 1-28.
Tobin, Martin, "Principles and Practice of Intensive Care Monitoring", 1998, in 30 pages.
Severinghaus, M.D., John, et al., Pulse Oximeter Failure Thresholds in Hypotension and Vasoconstriction, Anesthesiology, Sep. 1990, vol. 73, No. 3, pp. 532-537.
Pologe, Jonas A., "Pulse Oximetry: Technical Aspects of Machine Design", International Anesthesiology Clinics, Advances in Oxygen Monitoring, Fall, 1987, vol. 25, No. 3, pp. 137-153.
Tremper, Ph.D., Kevin et al., "Pulse Oximetry", Medical Intelligence Article, Anesthesiology, Jan. 1989, vol. 70, No. 1, pp. 98-108.
Bosque, PhD, Elena, "Symbiosis of nurse and machine through fuzzy logic: Improved specificity of a neonatal pulse oximeter alarm", Dec. 1995, vol. 18, Issue 2, pp. 67-75.
Paine, MPH, Christine, et al., "Systematic review of physiologic monitor alarm characteristics and pragmatic interventions to reduce alarm frequency" J Hosp Med., Feb. 2017, vol. 11, No. 2, pp. 136-144.
Top 10 Technology Hazards for 2012, Guidance Article, Nov. 2011, www.ecri.org, pp. 358-373.
Top 10 Technology Hazards for 2013, Health Devices, ECRI Institute, Nov. 2012, reprinted from vol. 41, Issue 11, in 25 pages.
Top 10 Health Technology Hazards for 2014, Health Devices, ECRI Institute, Nov. 2013, www.ecri.org/2014hazards, 1 page.
Masimo Advanced Alarm Performance: An Evidence-Based Approach to Reduce False Alarms and Nuisance Alarms, 2010, in 8 pages.
Complaint for Patent Infringement, *Masimo Corporation* v. *Sotera Wireless and Hon Hai Precision Industry Co., Ltd.*, Case No. 3:19-cv-01100-BAS-NLS, filed Jun. 12, 2019, in 385 pages.
Jun. 12, 2019 Complaint for Patent Infringement and Demand for Jury Trial, *Masimo Corporation* v. *Sotera Wireless and Hon Hai Precision Industry Co., Ltd.*, Case No. 3:19-cv-01100-BAS-NLS, 385 pages. [Uploaded in 2 parts].
Oct. 3, 2019 Defendant Sotera Wireless, Inc.'s Answer to Plaintiffs Complaint for Patent Infringement, *Masimo Corporation* v. *Sotera Wireless and Hon Hai Precision Industry Co., Ltd.*, Case No. 3:19-cv-01100-BAS-NLS, 26 pages.
Oct. 3, 2019 Defendant Hon Hai Precision Industry Co., Ltd.'s Notice of Motion and Motion Pursuant to Rule 12(b)(6) to Dismiss Plaintiff's Complaint, *Masimo Corporation* v. *Sotera Wireless and Hon Hai Precision Industry Co., Ltd.*, Case No. 3:19-cv-01100-BAS-NLS, 3 pages.
Oct. 3, 2019 Defendant Hon Hai Precision Industry Co., Ltd.'s Memorandum of Points and Authorities in Support of Motion Pursuant to Rule 12(b)(6) to Dismiss Plaintiff's Complaint, *Masimo Corporation* v. *Sotera Wireless and Hon Hai Precision Industry Co., Ltd.*, Case No. 3:19-cv-01100-BAS-NLS, 16 pages.
US 9,579,050, 02/2017, Al-Ali (withdrawn).
US 8,845,543, Diab et al. (withdrawn).
Coetzee, et al., "Noise-Resistant Pulse Oximetry Using a Synthetic Reference Signal," IEEE Transactions on Biomedical Engineering, IEEE Service Center, Piscataway, NJ, vol. 47, No. 8, dated Aug. 1, 2000.
Invitation to Pay Additional Fees document, including communication relating to the results of a partial Search Report issued in related application No. PCT/US2011/026545, dated Jun. 22, 2011, in 5 pages.
"Propaq Encore Vital Signs Monitor: Reference Guide," Welch Allyn, Inc., 2009 in 144 pages.

* cited by examiner

ADAPTIVE ALARM SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

PRIORITY CLAIM TO RELATED PROVISIONAL APPLICATIONS

[The present application claims priority benefit under 35 U.S.C. §119(e) to] *This is a reissue continuation application, meaning it is a reissue of U.S. Pat. No. 9,775,570, and is also a continuation of U.S. patent Reissue application Ser. No. 15/881,602, which is a reissue of U.S. Pat. No. 9,775,570, issued on Oct. 3, 2017 and titled "Adaptive Alarm System," which is a continuation of* U.S. patent application Ser. No. 13/037,184, filed Feb. 18, 2011 titled Adaptive Alarm System; *which claims priority benefit under 35 U.S.C. § 119(e) to* Provisional Patent Application Ser. No. 61/309,419, filed Mar. 1, 2010 titled Adaptive Threshold Alarm System; and U.S. Provisional Patent Application Ser. No. 61/328,630, filed Apr. 27, 2010 titled Adaptive Alarm System; all of the above-cited provisional patent applications are hereby incorporated by reference herein.

BACKGROUND OF THE INVENTION

Pulse oximetry systems for measuring constituents of circulating blood have gained rapid acceptance in a wide variety of medical applications, including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. A pulse oximetry sensor has light emitting diodes (LEDs), typically one emitting a red wavelength and one emitting an infrared (IR) wavelength, and a photodiode detector. The emitters and detector are typically attached to a finger, and the patient cable transmits drive signals to these emitters from the monitor. The emitters respond to the drive signals to transmit light into the fleshy fingertip tissue. The detector generates a signal responsive to the emitted light after attenuation by pulsatile blood flow within the fingertip. The patient cable transmits the detector signal to the monitor, which processes the signal to provide a numerical readout of physiological parameters such as oxygen saturation ($SpO_2$) and pulse rate.

SUMMARY OF THE INVENTION

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Masimo Laboratories, Irvine, Calif. (Masimo Labs) and all incorporated by reference herein. An advanced parameter measurement system that includes acoustic monitoring is described in U.S. Pat. Pub. No. 2010/0274099, filed Dec. 21, 2009, titled Acoustic Sensor Assembly, assigned to Masimo and incorporated by reference herein.

Advanced blood parameter measurement systems include Masimo Rainbow® SET, which provides measurements in addition to $SpO_2$, such as total hemoglobin (SpHb™) oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad87™ and Rad-57™ monitors, all available from Masimo. Advanced parameter measurement systems may also include acoustic monitoring such as acoustic respiration rate (RRa™) using a Rainbow Acoustic Sensor™ and Rad-87™ monitor, available from Masimo. Such advanced pulse oximeters, low noise sensors and advanced physiological parameter measurement systems have also gained rapid acceptance in a wide variety of medical applications, including surgical wards, intensive care and neonatal units, general wards, home care, physical training, and virtually all types of monitoring scenarios.

FIGS. 1-3 illustrate problems and issues associated with physiological parameter measurement systems having fixed threshold alarm schemas. FIG. 1 illustrates a lower-limit, fixed-threshold alarm schema with respect to an oxygen saturation ($SpO_2$) parameter. Two alarm thresholds, $D_L$ (delay) and $ND_L$ (no delay), are defined. If oxygen saturation falls below $D_L$ for a time delay greater than TD, an alarm is triggered. If oxygen saturation falls below $ND_L$ an alarm is immediately triggered. $D_L$ 120 is typically set around or somewhat above 90% oxygen saturation and $ND_L$ 130 is typically set at 5% to 10% below $D_L$. For example, say a person's oxygen saturation 110 drops below $D_L$ 120 at $t=t_1$ 162 and stays below $D_L$ for at least a time delay TD 163. This triggers a delayed alarm 140 at $t=t_2$ 164, where $t_2=t_1+$ TD. The alarm 140 remains active until oxygen saturation 110 rises above $D_L$ 120 at $t=t_3$ 166. As another example, say that oxygen saturation 110 then drops below $ND_L$ 130, which triggers an immediate alarm 150 at t=t4 168. The alarm 150 remains active until oxygen saturation 110 rises above $D_L$ 120 at $t=t_5$ 169.

FIG. 2 illustrates an upper-limit, fixed-threshold alarm schema with respect to an oxygen saturation ($SpO_2$) parameter. This alarm scenario is particularly applicable to the avoidance of ROP (retinopathy of prematurity). Again, two alarm thresholds, $D_U$ (delay) and $ND_U$ (no delay), are defined. $D_U$ 220 might be set at or around 85% oxygen saturation and $ND_U$ 230 might be set at or around 90% oxygen saturation. For example, a neonate's oxygen saturation 210 rises above $D_U$ 220 at $t=t_1$ 262 and stays above $D_U$ for at least a time delay TD 263. This triggers a delayed alarm 240 at $t=t_2$ 264, where $t_2=t_1+TD$. The alarm 240 remains active until oxygen saturation 210 falls below $D_U$ 220 at $t=t_3$ 166. Oxygen saturation 210 then rises above $ND_U$ 230, which triggers an immediate alarm 250 at $t=t_4$ 268. The alarm 250 remains active until oxygen saturation 210 falls below $D_U$ 220 at $t=t_5$ 269.

FIG. 3 illustrates a baseline drift problem with the fixed threshold alarm schema described above. A person's oxygen saturation is plotted on an oxygen saturation ($SpO_2$) versus time graph 300. In particular, during a first time interval $T_1$ 362, a person has an oxygen saturation 310 with a relatively stable "baseline" 312 punctuated by a shallow, transient desaturation event 314. This scenario may occur after the person has been on oxygen so that baseline oxygen saturation is near 100%. Accordingly, with a fixed threshold alarm 330 set at, say, 90%, the transient event 314 does not trigger a nuisance alarm. However, the effects of oxygen treatments wear off over time and oxygen saturation levels drift downward 350. In particular, during a second time interval $T_2$ 364, a person has an oxygen saturation 320 with a relatively stable baseline 322. The later baseline 322 is established at a substantially lower oxygen saturation than the earlier baseline 312. In this scenario, a shallow, transient desaturation event 324 now exceeds the alarm threshold 330 and results in a nuisance alarm. After many such nuisance alarms, a caregiver may lower the alarm threshold 330 to unsafe levels or turn off alarms altogether, significantly hampering the effectiveness of monitoring oxygen saturation.

A fixed threshold alarm schema is described above with respect to an oxygen saturation parameter, such as derived from a pulse oximeter. However, problematic fixed threshold alarm behavior may be exhibited in a variety of parameter measurement systems that calculate physiological parameters related to circulatory, respiratory, neurological, gastrointestinal, urinary, immune, musculoskeletal, endocrine or reproductive systems, such as the circulatory and respiratory parameters cited above, as but a few examples.

An adaptive alarm system, as described in detail below, advantageously provides an adaptive threshold alarm to solve false alarm and missed true alarm problems associated with baseline drift among other issues. For example, for a lower limit embodiment, an adaptive alarm system adjusts an alarm threshold downwards when a parameter baseline is established at lower values. Likewise, for an upper limit embodiment, the adaptive alarm system adjusts an alarm threshold upwards in accordance with baseline drift so as to avoid nuisance alarms. In an embodiment, the rate of baseline movement is limited so as to avoid masking of transients. In an embodiment, the baseline is established along upper or lower portions of a parameter envelop so as to provide a margin of safety in lower limit or upper limit systems, respectively.

One aspect of an adaptive alarm system is responsive to a physiological parameter so as to generate an alarm threshold that adapts to baseline drift in the parameter and reduce false alarms without a corresponding increase in missed true alarms. The adaptive alarm system has a parameter derived from a physiological measurement system using a sensor in communication with a living being. A baseline processor calculates a parameter baseline from an average value of the parameter. Parameter limits specify an allowable range of the parameter. An adaptive threshold processor calculates an adaptive threshold from the parameter baseline and the parameter limits. An alarm generator is responsive to the parameter and the adaptive threshold so as to trigger an alarm indicative of the parameter crossing the adaptive threshold. The adaptive threshold is responsive to the parameter baseline so as to increase in value as the parameter baseline drifts to a higher parameter value and to decrease in value as the parameter baseline drifts to a lower parameter value.

In various embodiments, the baseline processor has a sliding window that identifies a time slice of parameter values. A trend calculator determines a trend from an average of the parameter values in the time slice. A response limiter tracks only the relatively long-term transitions of the trend. A bias calculator deletes the highest parameter values in the time slice or the lowest parameter values in the time slice so as to adjust the baseline to either a lower value or a higher value, respectively. The adaptive threshold becomes less response to baseline drift as the baseline approaches a predefined parameter limit. A first adaptive threshold is responsive to lower parameter limits and a second adaptive threshold is responsive to upper parameter limits. The alarm generator is responsive to both positive and negative transients from the baseline according to the first adaptive threshold and the second adaptive threshold. The first adaptive threshold is increasingly responsive to negative transients and the second adaptive threshold is decreasingly responsive to positive transients as the baseline trends toward lower parameter values.

Another aspect of an adaptive alarm system measures a physiological parameter, establishes a baseline for the parameter, adjusts an alarm threshold according to drift of the baseline and triggers an alarm in response to the parameter measurement crossing the alarm threshold. In various embodiments, the baseline is established by biasing a segment of the parameter, calculating a biased trend from the biased segment and restricting the transient response of the biased trend. The alarm threshold is adjusted by setting a parameter limit and calculating a delta difference between the alarm threshold and the baseline as a linear function of the baseline according to the parameter limit. The delta difference is calculated by decreasing delta as the baseline drifts toward the parameter limit and increasing delta as the baseline drifts away from the parameter limit. A parameter limit is set by selecting a first parameter limit in relation to a delayed alarm and selecting a second parameter limit in relation to an un-delayed alarm. A segment of the parameter is biased by windowing the parameter measurements, removing a lower value portion of the windowed parameter measurements and averaging a remaining portion of the windowed parameter measurements. An upper delta difference between an upper alarm threshold and the baseline is calculated and a lower delta difference between a lower alarm threshold and the baseline is calculated.

A further aspect of an adaptive alarm system has a baseline processor that inputs a parameter and outputs a baseline according to a trend of the parameter. An adaptive threshold processor establishes an alarm threshold at a delta difference from the baseline. An alarm generator triggers an alarm based upon a parameter transient from the baseline crossing the alarm threshold. In various embodiments, a trend calculator outputs a biased trend and the baseline is responsive to the biased trend so as to reduce the size of a transient that triggers the alarm. A response limiter reduces baseline movement due to parameter transients. The adaptive threshold processor establishes a lower alarm threshold below the baseline and an upper alarm threshold above the baseline so that the alarm generator is responsive to both positive and negative transients from the baseline. The baseline processor establishes a lower baseline biased above the parameter trend and an upper baseline biased below the parameter trend. The lower alarm threshold is increasingly responsive to negative transients and the upper alarm threshold is decreasingly responsive to positive transients as the baseline trends toward lower parameter values.

DETAILED DESCRIPTION OF THE PREFERRED EMBODIMENTS

Figure 1:
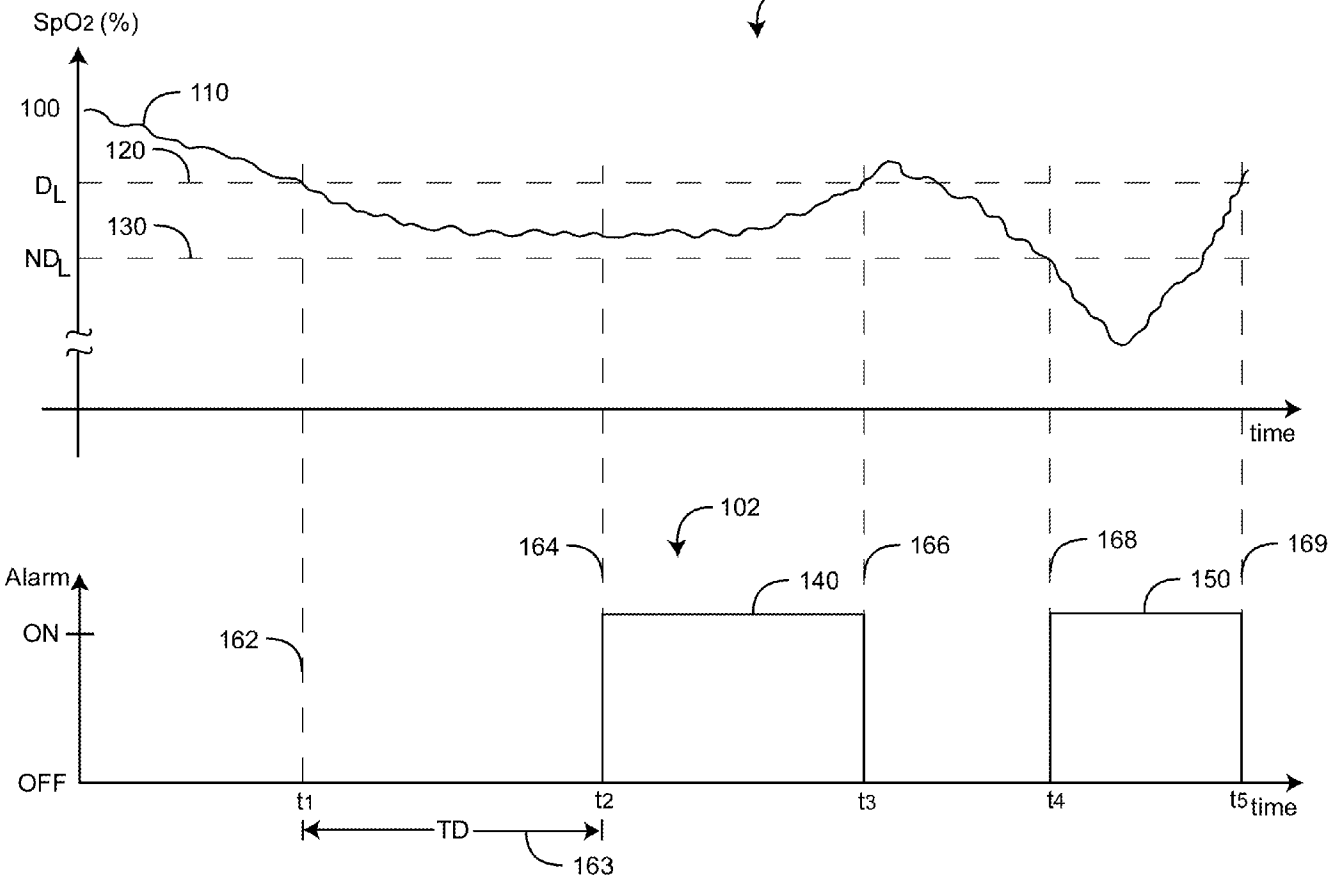
FIGS. 1-3 are exemplar graphs illustrating problems and issues associated with physiological parameter measurement systems having fixed threshold alarm schemas.
Figure 2:
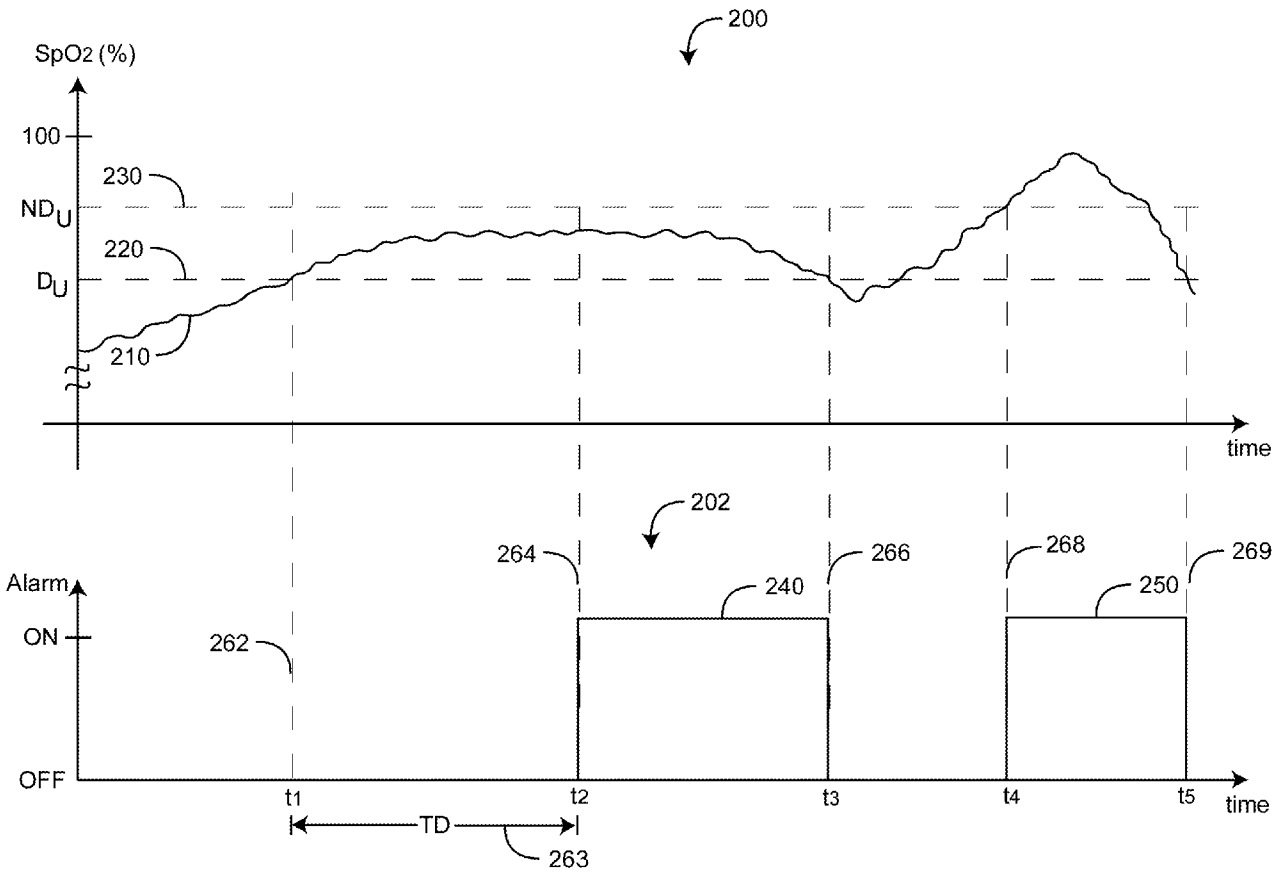
Figure 3:
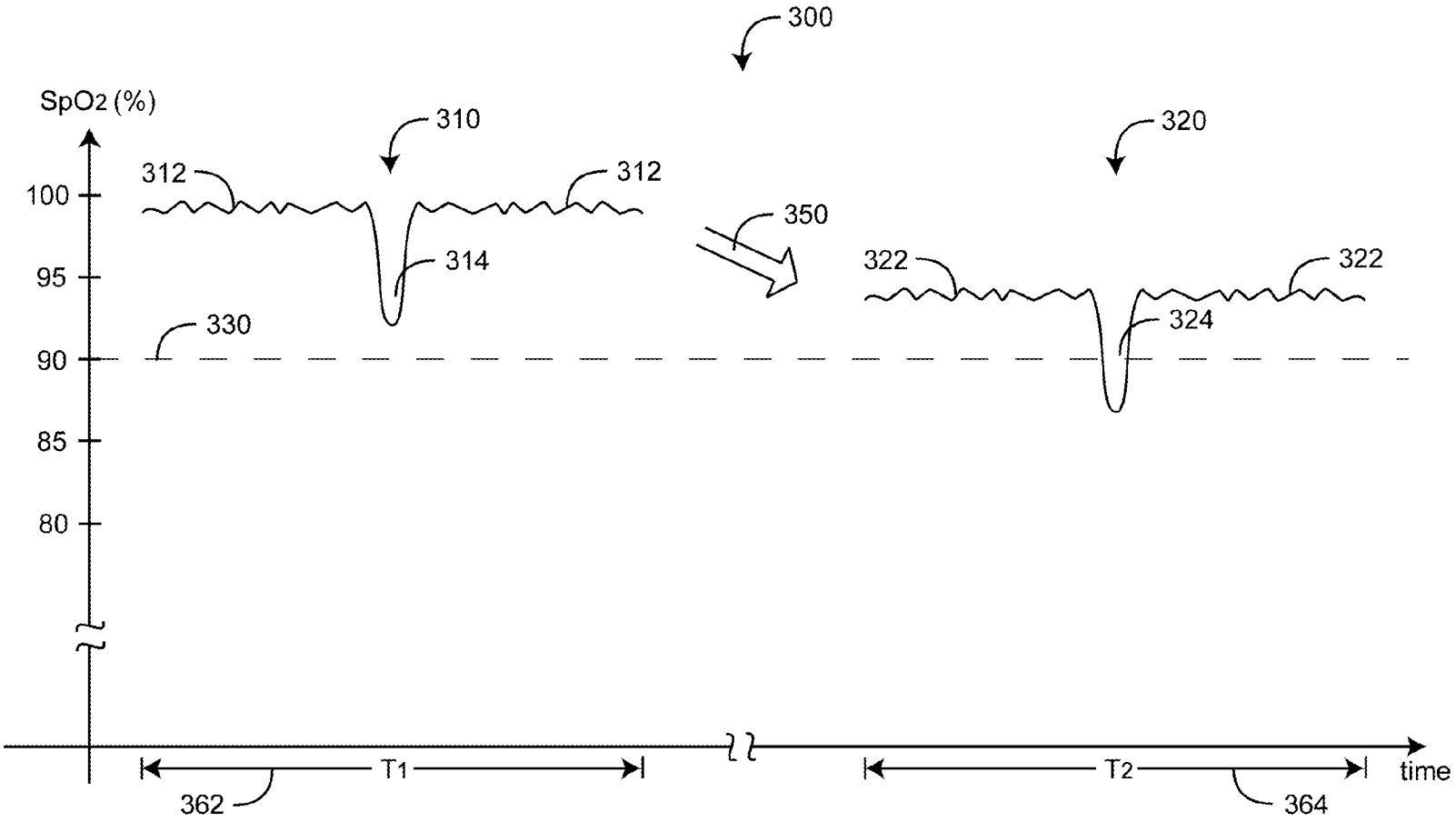
Figure 4A:
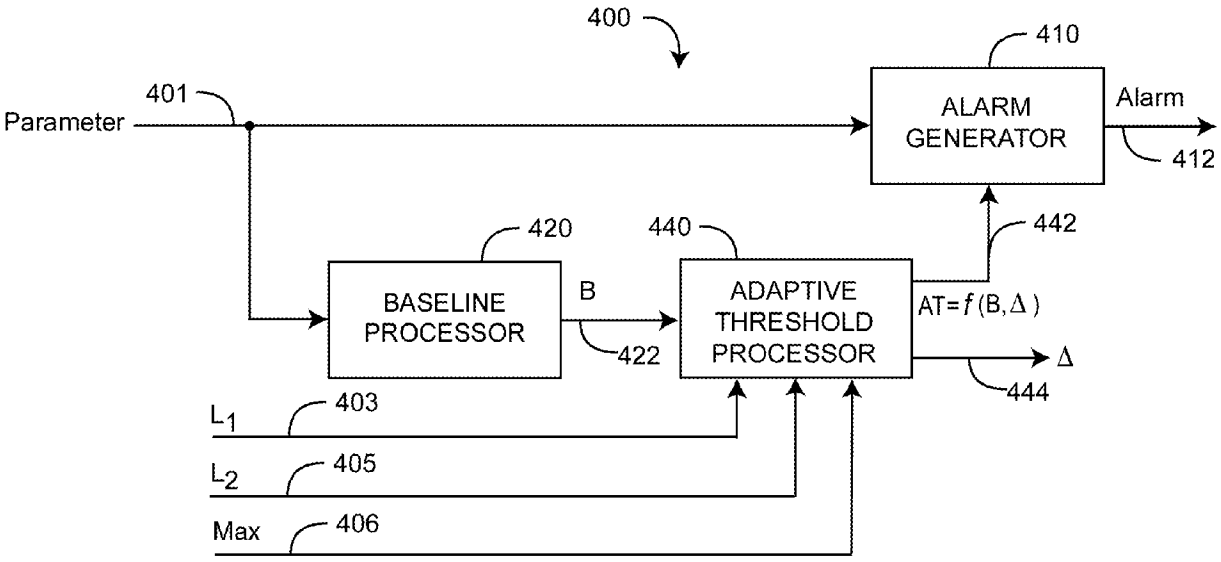
FIGS. 4A-B are general block diagrams of an adaptive alarm system having lower parameter limits.
Figure 4B:
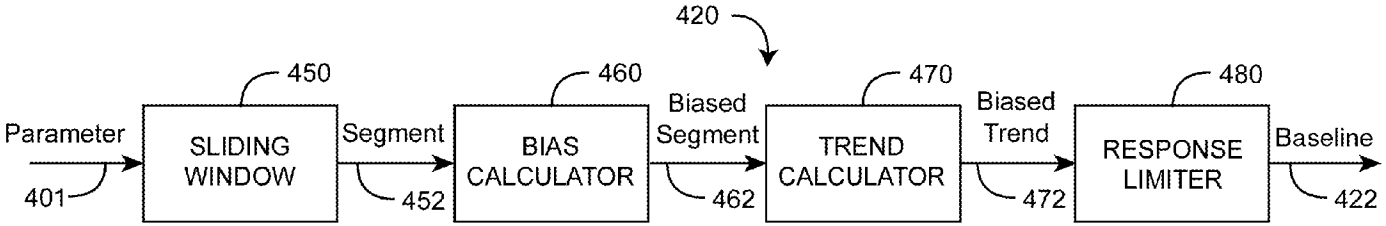

FIGS. 4A-B illustrate an adaptive alarm system 400 embodiment having lower parameter limits $L_1$ and $L_2$. As shown in FIG. 4A, the adaptive alarm system 400 has parameter 401, first limit ($L_1$) 403, second limit ($L_2$) 405 and maximum parameter value (Max) 406 inputs and generates a corresponding alarm 412 output. The parameter 401 input is generated by a physiological parameter processor, such as a pulse oximeter or an advanced blood parameter processor described above, as examples. The adaptive alarm system 400 has an alarm generator 410, a baseline processor 420, and an adaptive threshold processor 440. The alarm generator 410 has parameter 401 and adaptive threshold (AT) 442 inputs and generates the alarm 412 output accordingly. A baseline processor 420 has the parameter 401 input and generates a parameter baseline (B) 422 output. The baseline processor 420, is described in detail with respect to FIG. 4B, below. An adaptive threshold processor 440 has parameter baseline (B) 422, $L_1$ 403, $L_2$ 405 and Max 406 inputs and generates the adaptive threshold (AT) 442. The adaptive threshold processor 440 is described in detail with respect to FIGS. 5A-B, below.

As shown in FIG. 4A, in an embodiment $L_1$ 403 and $L_2$ 405 may correspond to conventional fixed alarm thresholds with and without an alarm time delay, respectively. For an adaptive threshold schema, however, $L_1$ 403 and $L_2$ 405 do not determine an alarm threshold per se, but are reference levels for determining an adaptive threshold (AT) 442. In an embodiment, $L_1$ 403 is an upper limit of the adaptive alarm threshold AT when the baseline is near the maximum parameter value (Max), and $L_2$ 405 is a lower limit of the adaptive alarm threshold, as described in detail with respect to FIGS. 5A-B, below. In an exemplar embodiment when the parameter is oxygen saturation, $L_1$ 403 is set at or around 90% and $L_2$ 405 is set at 5 to 10% below $L_1$, i.e. at 85% to 80% oxygen saturation. Many other $L_1$ and $L_2$ values may be used for an adaptive threshold schema as described herein.

Also shown in FIG. 4A, in an embodiment the alarm 412 output is triggered when the parameter 401 input falls below AT 442 and ends when the parameter 401 input rises above AT 442 or is otherwise cancelled. In an embodiment, the alarm 412 output is triggered after a time delay (TD), which may be fixed or variable. In an embodiment, the time delay (TD) is a function of the adaptive threshold (AT) 442. In an embodiment, the time delay (TD) is zero when the adaptive threshold (AT) is at the second lower limit ($L_2$) 405.

As shown in FIG. 4B, a baseline processor 420 embodiment has a sliding window 450, a bias calculator 460, a trend calculator 470 and a response limiter 480. The sliding window 450 inputs the parameter 401 and outputs a time segment 452 of the parameter 401. In an embodiment, each window incorporates a five minute span of parameter values. The bias calculator 460 advantageously provides an upward shift in the baseline (B) 422 for an additional margin of error over missed true alarms. That is, a baseline 422 is generated that tracks a higher-than-average range of parameter values, effectively raising the adaptive threshold AT slightly above a threshold calculated based upon a true parameter average, as shown and described in detail with respect to FIGS. 7-8, below. In an embodiment, the bias calculator 460 rejects a lower range of parameter values from each time segment 452 from the sliding window so as to generate a biased time segment 462.

Also shown in FIG. 4B, the trend calculator 470 outputs a biased trend 472 of the remaining higher range of parameter values in each biased segment 462. In an embodiment, the biased trend 462 is an average of the values in the biased time segment 462. In other embodiments, the biased trend 462 is a median or mode of the values in the biased time segment 462. The response limiter 480 advantageously limits the extent to which the baseline 422 output tracks the biased trend 472. Accordingly, the baseline 422 tracks only relatively longer-lived transitions of the parameter, but does not track (and hence mask) physiologically significant parameter events, such as oxygen desaturations for a $SpO_2$ parameter to name but one example. In an embodiment, the response limiter 480 has a low pass transfer function. In an embodiment, the response limiter 480 is a slew rate limiter.

Figure 5B:
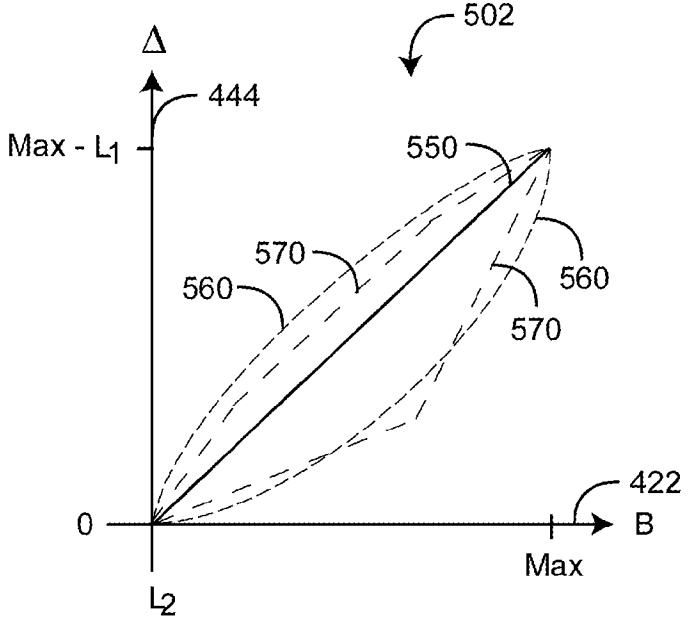
FIGS. 5A-B are a graph of a physiological parameter versus delta space and a graph of delta versus baseline, respectively, illustrating the relationship between a baseline, a lower-limit adaptive threshold and a variable difference delta between the baseline and the adaptive threshold.
Figure 5A:
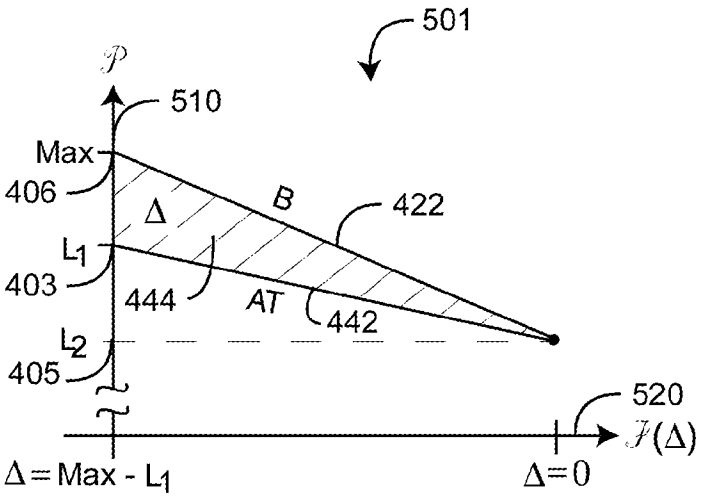

FIGS. 5A-B further illustrate an adaptive threshold processor 440 (FIG. 4A) having a baseline (B) 422 input and generating an adaptive threshold (AT) 442 output and a delta (Δ) 444 ancillary output according to parameter limits $L_1$ 403, $L_2$ 405 and Max 406, as described above. As shown in FIG. 5A, as the baseline (B) 422 decreases (increases) the adaptive threshold (AT) 444 monotonically decreases (increases) between $L_1$ 403 and $L_2$ 405. Further, as the baseline (B) 422 decreases (increases) the delta (Δ) 444 difference between the baseline (B) 422 and the adaptive threshold (AT) 442 monotonically decreases (increases) between Max−$L_1$ and zero.

As shown in FIG. 5B, the relationship between the delta (Δ) 444 and the baseline (B) 444 may be linear 550 (solid line), non-linear 560 (small-dash lines) or piecewise-linear (large-dash lines), to name a few. In an embodiment, the adaptive threshold processor 440 (FIG. 4A) calculates an adaptive threshold (AT) 442 output in response to the baseline (B) 422 input according to a linear relationship. In a linear embodiment, the adaptive threshold processor 440 (FIG. 4A) calculates the adaptive threshold (AT) 442 according to EQS. 1-2:

$$\Delta = -\left(\frac{\text{Max} - L_1}{\text{Max} - L_2}\right)(\text{Max} - B) + (\text{Max} - L_1) \tag{1}$$

$$AT = B - \Delta \tag{2}$$

where Δ=Max−$L_1$ @ B=Max; Δ=0 @ B=$L_2$
and where AT=$L_1$ @ B=Max; AT=$L_2$ @ B=$L_2$, accordingly.

Figure 6:
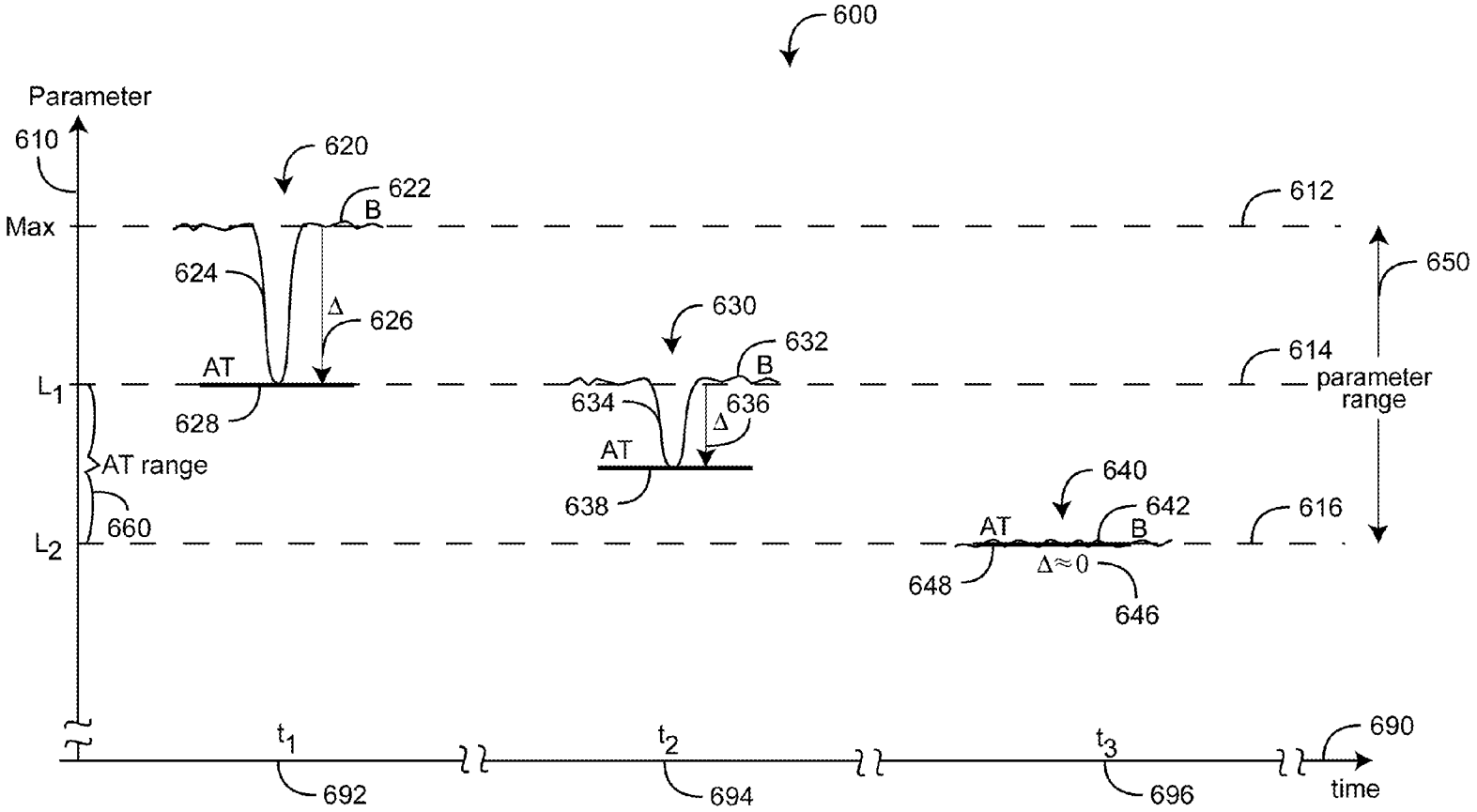
FIG. 6 is an exemplar graph of a physiological parameter versus time illustrating an adaptive alarm system having a lower-limit adaptive threshold.

FIG. 6 illustrates the operational characteristics an adaptive alarm system 400 (FIG. 4A) having parameter limits Max 612, $L_1$ 614 and $L_2$ 616 and an alarm responsive to a baseline (B) 622, 632, 642; an adaptive threshold (AT) 628, 638, 648; and a corresponding Δ 626, 636, 646 according to EQS. 1-2, above. In particular, a physiological parameter 610 is graphed versus time 690 for various time segments $t_1$, $t_2$, $t_3$ 692-696. The parameter range (PR) 650 is:

$$PR = \text{Max} - L_2 \tag{3}$$

and the adaptive threshold range (ATR) 660 is:

$$ATR = L_1 - L_2 \tag{4}$$

As shown in FIG. 6, during a first time period $t_1$ 692, a parameter segment 620 has a baseline (B) 622 at about Max 612. As such, Δ 626=Max−$L_1$ and the adaptive threshold (AT) 628 is at about $L_1$ 614. Accordingly, a transient 624 having a size less than Δ 626 does not trigger the alarm 412 (FIG. 4A).

Also shown in FIG. 6, during a second time period $t_2$ 694, a parameter segment 630 has a baseline (B) 632 at about $L_1$ 614. As such, Δ 636 is less than Max−$L_1$ and the adaptive threshold (AT) 638 is between $L_1$ and $L_2$. Accordingly, a smaller transient 634 will trigger the alarm as compared to a transient 624 in the first time segment.

Further shown in FIG. 6, during a third time period $t_3$ 696, a parameter segment 640 has a baseline (B) 642 at about $L_2$ 616. As such, Δ 646 is about zero and the adaptive threshold (AT) 648 is at about $L_2$. Accordingly, even a small negative transient will trigger the alarm. As such, the behavior of the alarm threshold AT 628, 638, 648 advantageously adapts to higher or lower baseline values so as to increase or decrease the size of negative transients that trigger or do not trigger the alarm 412 (FIG. 4A).

Figure 7:
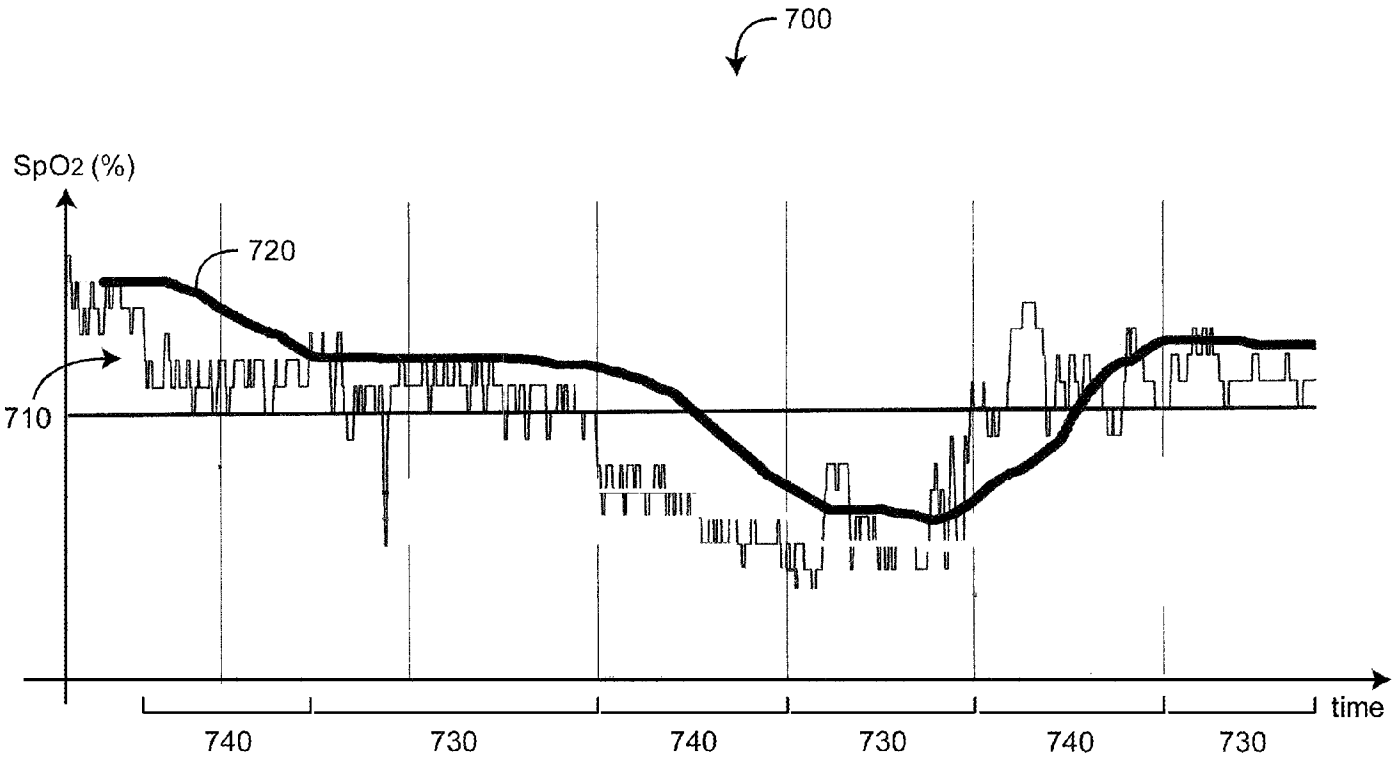
FIG. 7 is a graph of oxygen saturation versus time illustrating a baseline for determining an adaptive threshold.

FIG. 7 is a parameter versus time graph 700 illustrating the characteristics of an adaptive alarm system 400 (FIGS. 4A-B), as described with respect to FIGS. 4-6, above, where the parameter is oxygen saturation ($SpO_2$). The graph 700 has a $SpO_2$ trace 710 and a superimposed baseline trace 720. The graph 700 also delineates tracking periods 730, where the baseline 720 follows the upper portions of $SpO_2$ values, and lagging periods 740, where the baseline 720 does not follow transient $SpO_2$ events. The tracking time periods 730 illustrate that the baseline 720 advantageously tracks at the higher range of $SpO_2$ values 710 during relatively stable (flat) periods, as described above. Lagging time periods 740 illustrate that the baseline 720 is advantageously limited in response to transient desaturation events so that significant desaturations fall below an adaptive threshold (not shown) and trigger an alarm accordingly.

Figure 8:
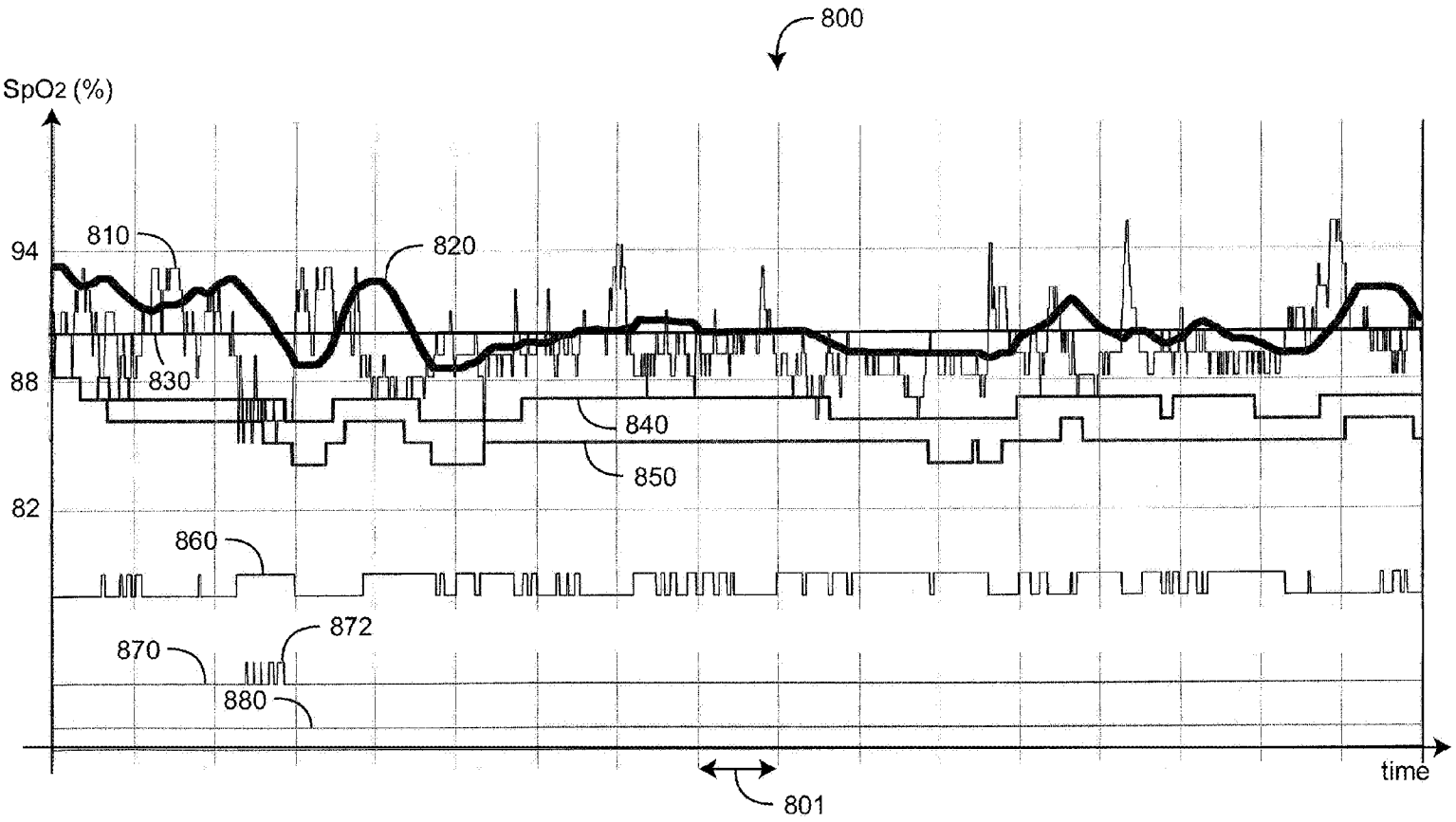
FIG. 8 is a graph of oxygen saturation versus time comparing adaptive-threshold alarm performance with fixed-threshold alarm performance.

FIG. 8 is a parameter versus time graph 800 illustrating characteristics of an adaptive alarm system 400 (FIGS. 4A-B), as described with respect to FIGS. 4-6, above, where the parameter is oxygen saturation ($SpO_2$). Vertical axis ($SpO_2$) resolution is 1%. The time interval 801 between vertical hash marks is five minutes. The graph 800 has a $SpO_2$ trace 810 and a baseline trace 820. The graph 800 also has a fixed threshold trace 830, a first adaptive threshold (AT) trace 840 and a second AT trace 850. The graph 800 further has a fixed threshold alarm trace 860, a first adaptive threshold alarm trace 870 and a second adaptive threshold alarm trace 880. In this example, $L_1$ is 90% and $L_2$ is 85% for the first AT trace 840 and first AT alarm trace 870. $L_2$ is 80% for a second AT trace 850 and a second AT alarm trace 880. The fixed threshold 830 results in many nuisance alarms 860. By comparison, the adaptive threshold alarm with $L_2$=85% has just one time interval of alarms 872 during a roughly 6% desaturation period (from 92% to 86%). The adaptive threshold alarm with $L_2$=80%, has no alarms during the 1 hour 25 minute monitoring period.

Figure 9A:
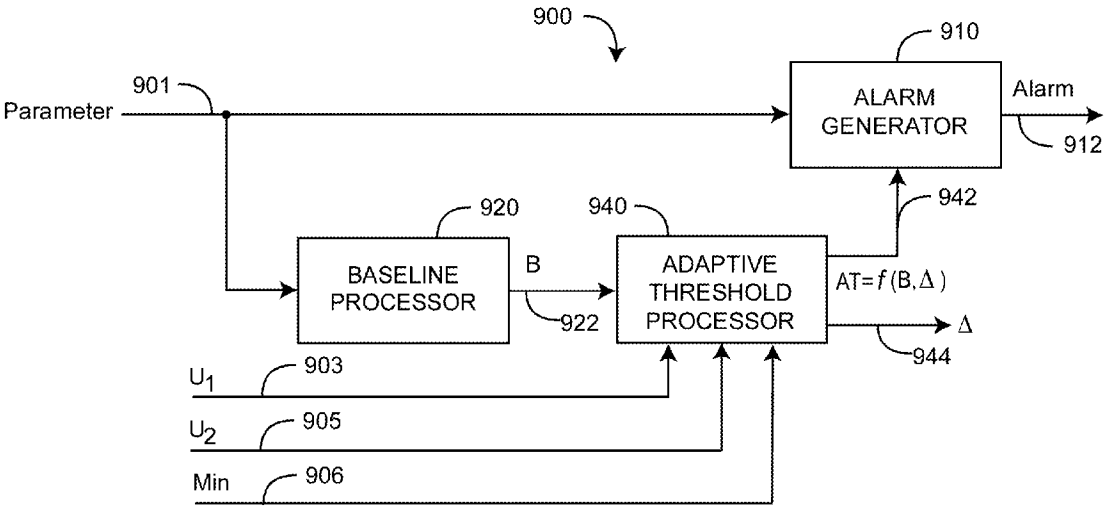
FIGS. 9A-B are general block diagrams of an adaptive alarm system having upper parameter limits.
Figure 9B:
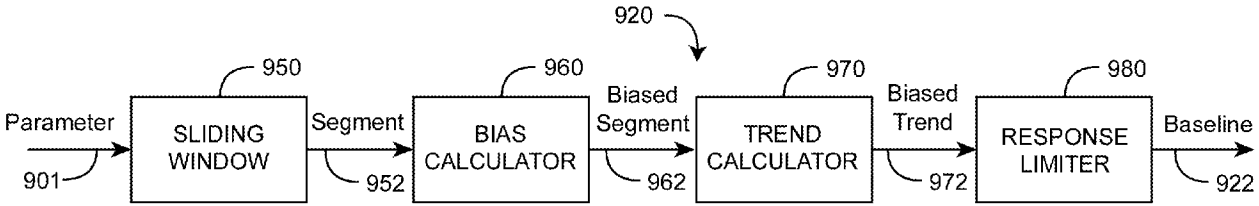

FIGS. 9A-B illustrate an adaptive alarm system 900 embodiment having upper parameter limits $U_1$ and $U_2$. As shown in FIG. 9A, the adaptive alarm system 900 has parameter 901, first limit ($U_1$) 903, second limit ($U_2$) 905 and minimum parameter value (Min) 906 inputs and generates a corresponding alarm 912 output. The parameter 901 input is generated by a physiological parameter processor, such as a pulse oximeter or an advanced blood parameter processor described above, as examples. The adaptive alarm system 900 has an alarm generator 910, a baseline processor 920, and an adaptive threshold processor 940. The alarm generator 910 has parameter 901 and adaptive threshold (AT) 942 inputs and generates the alarm 912 output accordingly. A baseline processor 920 has the parameter 901 input and generates a parameter baseline (B) 922 output. The baseline processor 920, is described in detail with respect to FIG. 9B, below. An adaptive threshold processor 940 has parameter baseline (B) 922, $U_1$ 903, $U_2$ 905 and Min 906 inputs and generates the adaptive threshold (AT) 942. The adaptive threshold processor 940 is described in detail with respect to FIGS. 10A-B, below.

As shown in FIG. 9A, in an embodiment $U_1$ 903 and $U_2$ 905 may correspond to conventional fixed alarm thresholds with and without an alarm time delay, respectively. For an adaptive threshold schema, however, $U_1$ 903 and $U_2$ 905 do not determine an alarm threshold per se, but are reference levels for determining an adaptive threshold (AT) 942. In an embodiment, $U_1$ 903 is a lower limit of the adaptive alarm threshold AT when the baseline is near the minimum parameter value (Min), and $U_2$ 905 is an upper limit of the adaptive alarm threshold, as described in detail with respect to FIGS. 10A-B, below. In an exemplar embodiment when the parameter is oxygen saturation, $U_1$ 903 is set at or around 85% and $U_2$ 905 is set at or around 90% oxygen saturation. Many other $U_1$ and $U_2$ values may be used for an adaptive threshold schema as described herein.

Also shown in FIG. 9A, in an embodiment the alarm 912 output is triggered when the parameter 901 input rises above AT 942 and ends when the parameter 901 input falls below AT 942 or is otherwise cancelled. In an embodiment, the alarm 912 output is triggered after a time delay (TD), which may be fixed or variable. In an embodiment, the time delay (TD) is a function of the adaptive threshold (AT) 942. In an embodiment, the time delay (TD) is zero when the adaptive threshold (AT) is at the second upper limit ($U_2$) 905.

As shown in FIG. 9B, a baseline processor 920 embodiment has a sliding window 950, a bias calculator 960, a trend calculator 970 and a response limiter 980. The sliding window 950 inputs the parameter 901 and outputs a time segment 952 of the parameter 901. In an embodiment, each window incorporates a five minute span of parameter values. The bias calculator 960 advantageously provides a downward shift in the baseline (B) 922 for an additional margin of error over missed true alarms. That is, a baseline 922 is generated that tracks a lower-than-average range of parameter values, effectively lowering the adaptive threshold AT slightly below a threshold calculated based upon a true parameter average. In an embodiment, the bias calculator 960 rejects an upper range of parameter values from each time segment 952 from the sliding window so as to generate a biased time segment 962.

Also shown in FIG. 9B, the trend calculator 970 outputs a biased trend 972 of the remaining lower range of parameter values in each biased segment 962. In an embodiment, the biased trend 962 is an average of the values in the biased time segment 962. In other embodiments, the biased trend 962 is a median or mode of the values in the biased time segment 962. The response limiter 980 advantageously limits the extent to which the baseline 922 output tracks the biased trend 972. Accordingly, the baseline 922 tracks only relatively longer-lived transitions of the parameter, but does not track (and hence mask) physiologically significant parameter events, such as oxygen desaturations for a $SpO_2$ parameter to name but one example. In an embodiment, the response limiter 980 has a low pass transfer function. In an embodiment, the response limiter 980 is a slew rate limiter.

Figure 10B:
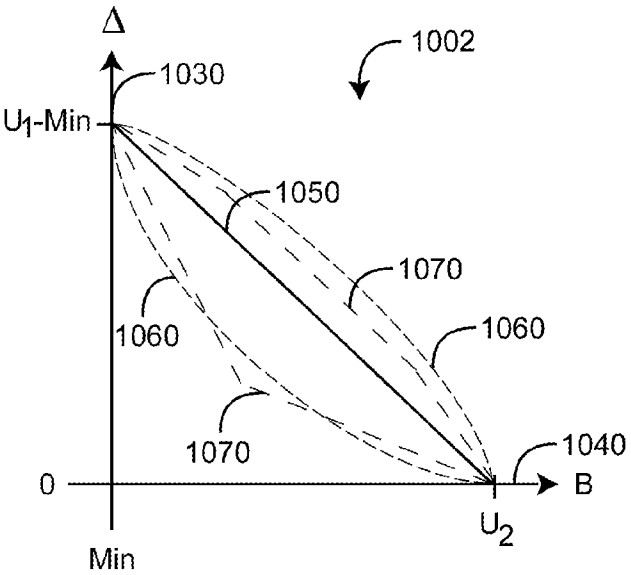
FIGS. 10A-B are a graph of a physiological parameter versus delta space and a graph of delta versus baseline, respectively, illustrating the relationship between a baseline, an upper-limit adaptive threshold and a variable delta difference between the baseline and the adaptive threshold.
Figure 10A:
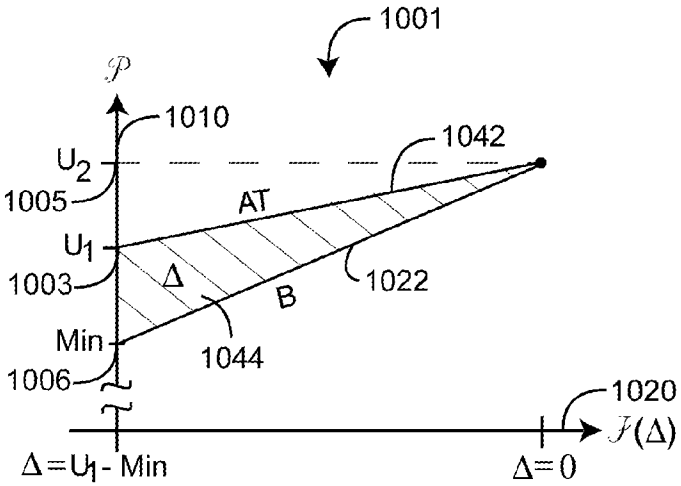

FIGS. 10A-B further illustrate an adaptive threshold processor 940 (FIG. 9A) having a baseline (B) 922 input and generating an adaptive threshold (AT) 942 output and a delta (Δ) 944 ancillary output according to parameter limits $U_1$ 903, $U_2$ 905 and Min 906, as described above. As shown in FIG. 10A, as the baseline (B) 922 decreases (increases) the adaptive threshold (AT) 944 monotonically decreases (increases) between $U_1$ 903 and $U_2$ 905. Further, as the baseline (B) 922 decreases (increases) the delta (Δ) 944 difference between the baseline (B) 922 and the adaptive threshold (AT) 942 monotonically decreases (increases) between Min–$U_1$ and zero.

As shown in FIG. 10B, the relationship between the delta (Δ) 944 and the baseline (B) 944 may be linear 550 (solid line), non-linear 560 (small-dash lines) or piecewise-linear (large-dash lines), to name a few. In an embodiment, the adaptive threshold processor 940 (FIG. 9A) calculates an adaptive threshold (AT) 942 output in response to the baseline (B) 922 input according to a linear relationship. In a linear embodiment, the adaptive threshold processor 940 (FIG. 9A) calculates the adaptive threshold (AT) 942 according to EQS. 5-6:

$$\Delta = -\left(\frac{U_1 - \text{Min}}{U_2 - \text{Min}}\right)(B - \text{Min}) + (U_1 - \text{Min}) \tag{5}$$

$$AT = B + \Delta \tag{6}$$

where $\Delta = U_1 - \text{Min}$ @ B=Min; $\Delta = 0$ @ $B = U_2$
and where $AT = U_1$ @ B=Min; $AT = U_2$ @ $B = U_2$, accordingly.

Figure 11:
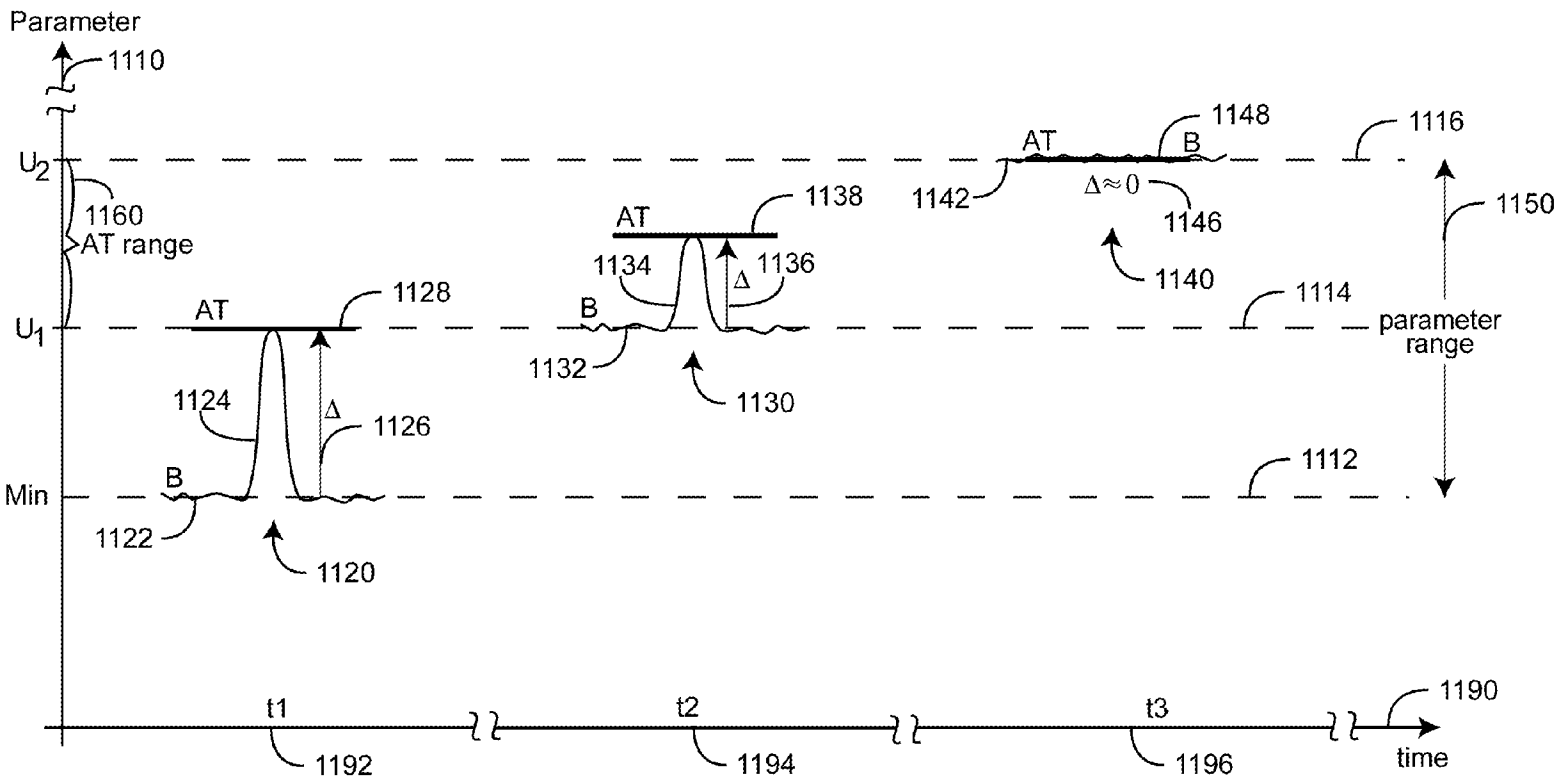
FIG. 11 is an exemplar graph of a physiological parameter versus time illustrating an adaptive alarm system having an upper-limit adaptive threshold.

FIG. 11 illustrates the operational characteristics an adaptive alarm system 900 (FIG. 9A) having parameter limits Min 1112, $U_1$ 1114 and $U_2$ 1116 and an alarm responsive to a baseline (B) 1122, 1132, 1142; an adaptive threshold (AT) 1128, 1138, 1148; and a corresponding Δ 1126, 1136, 1146 according to EQS. 5-6, above. In particular, a physiological parameter 1110 is graphed versus time 1190 for various time segments $t_1$, $t_2$, $t_3$ 1192-1196. The parameter range (PR) 1150 is:

$$PR = U_2 - \text{Min} \tag{7}$$

and the adaptive threshold range (ATR) 1160 is:

$$ATR = U_2 - U_1 \tag{8}$$

As shown in FIG. 11, during a first time period $t_1$ 1192, a parameter segment 1120 has a baseline (B) 1122 at about Min 1112. As such, Δ 1126=$U_1$–Min and the adaptive threshold (AT) 1128 is at about $U_1$ 1114. Accordingly, a transient 1124 having a size less than Δ 1126 does not trigger the alarm 912 (FIG. 9A).

Also shown in FIG. 11, during a second time period $t_2$ 1194, a parameter segment 1130 has a baseline (B) 1132 at about $U_1$ 1114. As such, Δ 1136 is less than $U_1$–Min and the adaptive threshold (AT) 1138 is between $U_1$ and $U_2$. Accordingly, a smaller transient 1134 will trigger the alarm as compared to a transient 1124 in the first time segment.

Further shown in FIG. 11, during a third time period $t_3$ 1196, a parameter segment 1140 has a baseline (B) 1142 at about $U_2$ 1116. As such, Δ 1146 is about zero and the adaptive threshold (AT) 1148 is at about $U_2$. Accordingly, even a small positive transient will trigger the alarm. As such, the behavior of the alarm threshold AT 1128, 1138, 1148 advantageously adapts to higher or lower baseline values so as to increase or decrease the size of positive transients that trigger or do not trigger the alarm 912 (FIG. 9A).

Figure 12A:
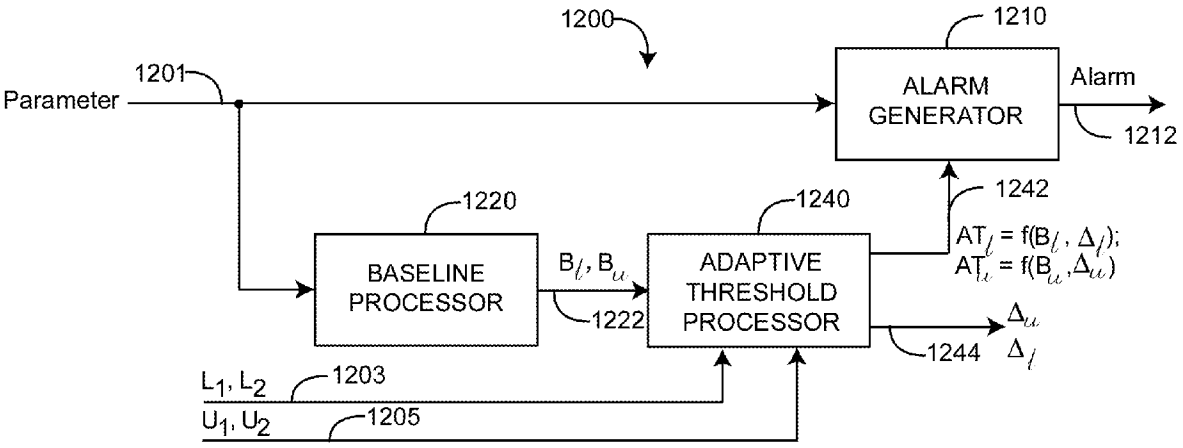
FIGS. 12A-B are general block diagrams of an adaptive alarm system having both lower alarm limits and upper alarm limits.
Figure 12B:
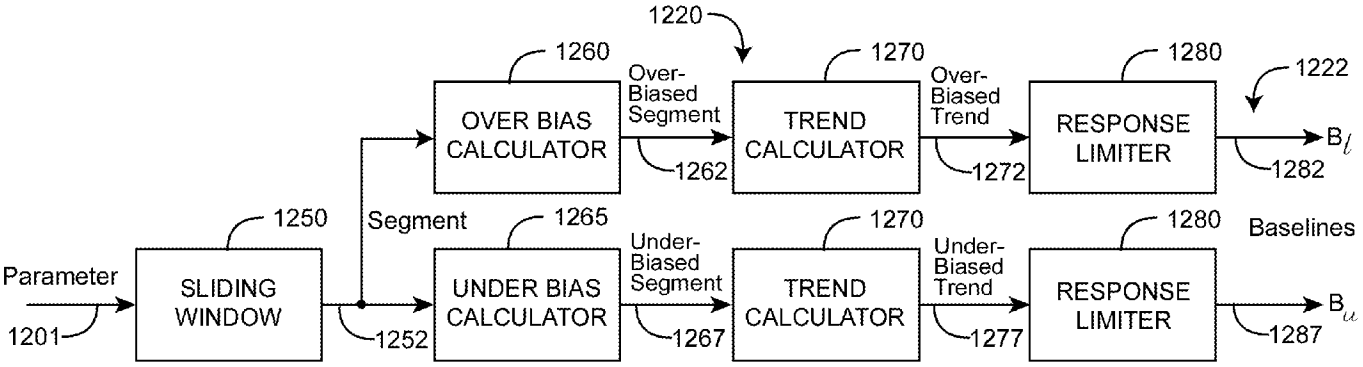

FIGS. 12A-B illustrate an adaptive alarm system 1200 embodiment having lower limits $L_1$, $L_2$ 1203, such as described with respect to FIGS. 4A-B above, or upper limits $U_1$, $U_2$ 1205 such as described with respect to FIGS. 9A-B above, or both. As shown in FIG. 12A, the adaptive alarm system 1200 has parameter 1201, lower limit 1203 and upper limit 1205 inputs and generates a corresponding alarm 1212 output. The parameter 1201 input is generated by a physiological parameter processor, such as a pulse oximeter or an advanced blood parameter processor described above, as examples. The adaptive alarm system 1200 has an alarm generator 1210, a baseline processor 1220 and an adaptive threshold processor 1240. The alarm generator 1210 has parameter 1201 and adaptive threshold (AT) 1242 inputs and generates the alarm 1212 output accordingly. A baseline processor 1220 has the parameter 1201 input and generates one or more parameter baseline 1222 outputs. The baseline processor 1220, is described in detail with respect to FIG.

12B, below. An adaptive threshold processor 1240 has parameter baseline 1222, lower limit $L_1$, $L_2$ 1203 and upper limit $U_1$, $U_2$ 1205 inputs and generates lower and upper adaptive threshold $AT_l$, $AT_u$ 1242 outputs. The adaptive threshold processor 1240 also generates ancillary upper and lower delta 1244 outputs. The adaptive threshold processor 1240 is described in detail with respect to FIGS. 13A-E, below.

As shown in FIG. 12A, in an embodiment $L_1$, $L_2$ 1203 and $U_1$, $U_2$ 1205 may correspond to conventional fixed alarm thresholds with an alarm delay ($L_1$, $U_1$) and without an alarm delay ($L_2$, $U_2$). For an adaptive threshold schema, however, these limits 1203, 1205 do not determine an alarm threshold per se, but are reference levels for determining lower and upper adaptive thresholds $AT_l$, $AT_u$ 1242.

Also shown in FIG. 12A, in an embodiment the alarm 1212 output is triggered when the parameter 1201 input falls below $AT_l$ 1242 and ends when the parameter 1201 input rises above $AT_l$ 1242 or the alarm is otherwise cancelled. Further, the alarm 1212 output is triggered when the parameter 1201 input rises above $AT_u$ 1242 and ends when the parameter 1201 input falls below $AT_u$ 1242 or the alarm is otherwise cancelled. In an embodiment, the alarm 1212 output is triggered after a time delay (TD), which may be fixed or variable. In an embodiment, the time delay (TD) is a function of the adaptive thresholds ($AT_l$, $AT_u$) 1242. In an embodiment, the time delay (TD) is zero when the lower adaptive threshold ($AT_l$) 1242 is at the second lower limit ($L_2$) 1203 or when the upper adaptive alarm threshold $AT_u$ 1242 is at the second upper limit ($U_2$) 1205.

As shown in FIG. 12B, a baseline processor 1220 embodiment has a sliding window 1250, an over-bias calculator 1260, an under-bias calculator 1265, trend calculators 1270 and response limiters 1280. The sliding window 1250 inputs the parameter 1201 and outputs a time segment 1252 of the parameter 1201. In an embodiment, each window incorporates a five minute span of parameter 1201 values.

Also shown in FIG. 12B, the over-bias calculator 1260 advantageously provides an upward shift in the lower baseline ($B_l$) 1282 for an additional margin of error over missed lower true alarms. That is, a lower baseline ($B_l$) 1282 is generated that tracks a higher-than-average range of parameter values, effectively raising the lower adaptive threshold $AT_l$ slightly above a threshold calculated based upon a true parameter average. In an embodiment, the over-bias calculator 1260 rejects a lower range of parameter values from each time segment 1252 of the sliding window 1250 so as to generate an over-biased time segment 1262.

Further shown in FIG. 12B, the under-bias calculator 1265 advantageously provides a downward shift in the upper baseline ($B_u$) 1287 for an additional margin of error over missed upper true alarms. That is, an upper baseline ($B_u$) 1287 is generated that tracks a lower-than-average range of parameter values, effectively lowering the upper adaptive threshold $AT_u$ slightly below a threshold calculated based upon a true parameter average. In an embodiment, the under-bias calculator 1267 rejects an upper range of parameter values from each time segment 1252 of the sliding window 1250 so as to generate an under-biased time segment 1267.

Additionally shown in FIG. 12B, the trend calculator 1270 outputs an over-biased trend 1272 of the remaining higher range of parameter values in each over-biased segment 1262. Further, the trend calculator 1270 outputs an under-biased trend 1277 of the remaining lower range of parameter values in each under-biased segment 1267. In an embodiment, the biased trends 1272, 1277 are each an average of the values in the corresponding biased time segments 1262, 1267. In other embodiments, the biased trends 1272, 1277 are each a median or mode of the values in the corresponding biased time segments 1262, 1267. The response limiter 1280 advantageously limits the extent to which the baseline 1222 outputs track the biased trends 1272, 1277. Accordingly, the baseline 1222 outputs track only relatively longer-lived transitions of the parameter 1201, but do not track (and hence mask) physiologically significant parameter events. In an embodiment, the response limiter 1280 has a low pass transfer function. In an embodiment, the response limiter 1280 is a slew rate limiter.

Figure 13A:
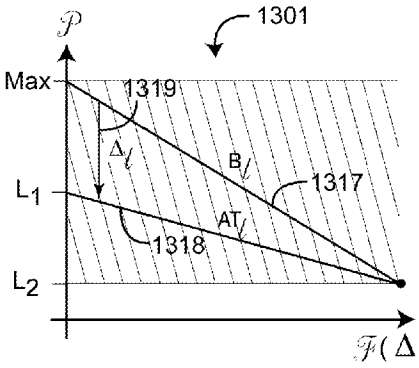
FIGS. 13A-E are physiological parameter versus delta space graphs illustrating a lower-limit adaptive threshold, an upper-limit adaptive threshold, and a combined lower- and upper-limit adaptive threshold in various delta spaces.

FIGS. 13A-E illustrate parameter (P) operating ranges and ideal ranges in view of both lower and upper parameter limits. As shown in FIG. 13A, as the baseline ($B_l$) 1317 decreases (increases) the adaptive threshold ($AT_l$) 1318 monotonically decreases (increases) between $L_1$ and $L_2$. Further, as the baseline ($B_l$) 1317 decreases (increases) the delta ($\Delta_l$) 1319 difference between the baseline ($B_l$) 1317 and the adaptive threshold ($AT_l$) 1318 monotonically decreases (increases) between Max−$L_1$ and 0.

Figure 13B:
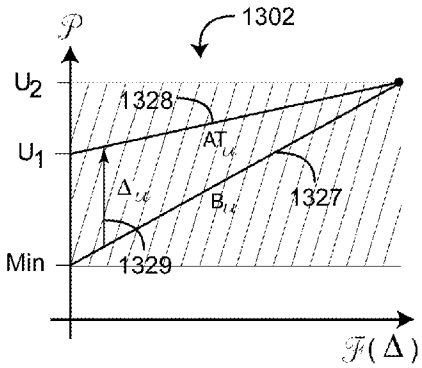

As shown in FIG. 13B, as the baseline ($B_u$) 1327 increases (decreases) the adaptive threshold ($AT_u$) 1328 monotonically increases (decreases) between $U_1$ and $U_2$. Further, as the baseline ($B_u$) 1327 increases (decreases) the delta ($\Delta_u$) 1329 difference between the adaptive threshold ($AT_u$) 1328 and the baseline ($B_u$) 1327 monotonically decreases (increases) between Min−$U_1$ and 0.

Figure 13C:
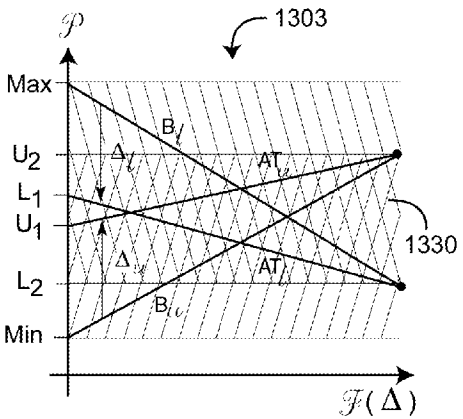

As shown in FIG. 13C, combining FIGS. 13A-B, the parameter (P) operating range is bounded by the overlapping regions of 13A and 13B 1330 having an upper bound of $U_2$ and a lower bound of $L_2$. In particular, $L_1$, $L_2$ are the upper and lower limits of the lower adaptive alarm threshold $AT_l$; and $U_2$, $U_1$ are the upper and lower limits of the upper adaptive alarm threshold $AT_u$.

Figure 13D:
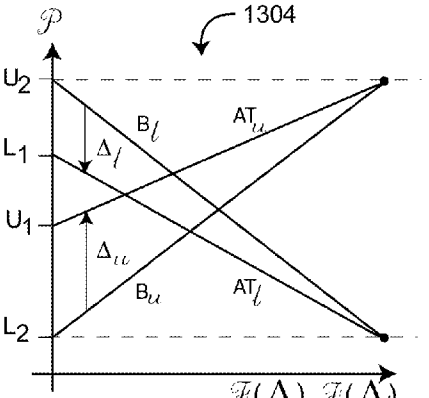
Figure 13E:
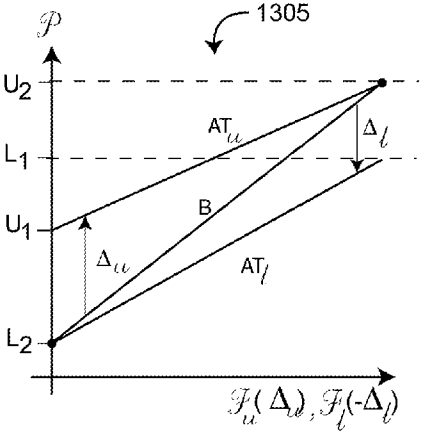

FIG. 13D illustrates parameter (P) versus the overlapping independent delta domains $F_u$, $F_l$ for upper and lower baselines $B_u$, $B_l$; adaptive thresholds $AT_u$, $AT_l$ and deltas $\Delta_u$, $\Delta_l$, based upon FIGS. 13A-C. FIG. 13E illustrates parameter (P) versus the overlapping independent delta domains $F_u$, $F_l$ (reversed); for upper and lower baselines $B_u$, $B_l$; adaptive thresholds $AT_u$, $AT_l$ and deltas $\Delta_u$, $\Delta_l$, As shown in FIG. 13E, the equations for bi-lateral adaptive thresholds are:

$$\Delta_u = -\left(\frac{U_1 - L_2}{U_2 - L_2}\right)(B - L_2) + (U_1 - L_2) \tag{9}$$

$$AT_u = B + \Delta_u \tag{10}$$

where $\Delta_u = U_1 - L_2$ @ $B = L_2$; and $\Delta_u = 0$ @ $B = U_2$; and where $AT_u = U_1$ @ $B = L_2$; and $AT_u = U_2$ @ $B = U_2$.
Further:

$$\Delta_l = \left(\frac{U_2 - L_1}{U_2 - L_2}\right)(B - L_2) \tag{11}$$

$$AT_l = B - \Delta_l \tag{12}$$

where $\Delta_l = U_2 - L_1$ @ $B = U_2$; and $\Delta_l = 0$ @ $B = L_2$; and where $AT_l = L_1$ @ $B = U_2$; $AT_l = L_2$ @ $B = L_2$.

Although shown as a linear relationship, in general:

$$\Delta_l = f_1(B); \Delta_u = f_2(B)$$

That is, $\Delta_l$ and $\Delta_u$ can each be a linear function of B, a non-linear function of B or a piecewise linear function of B, to name a few, in a manner similar to that described with respect to FIGS. 5B and 10B, above.

Figure 14:
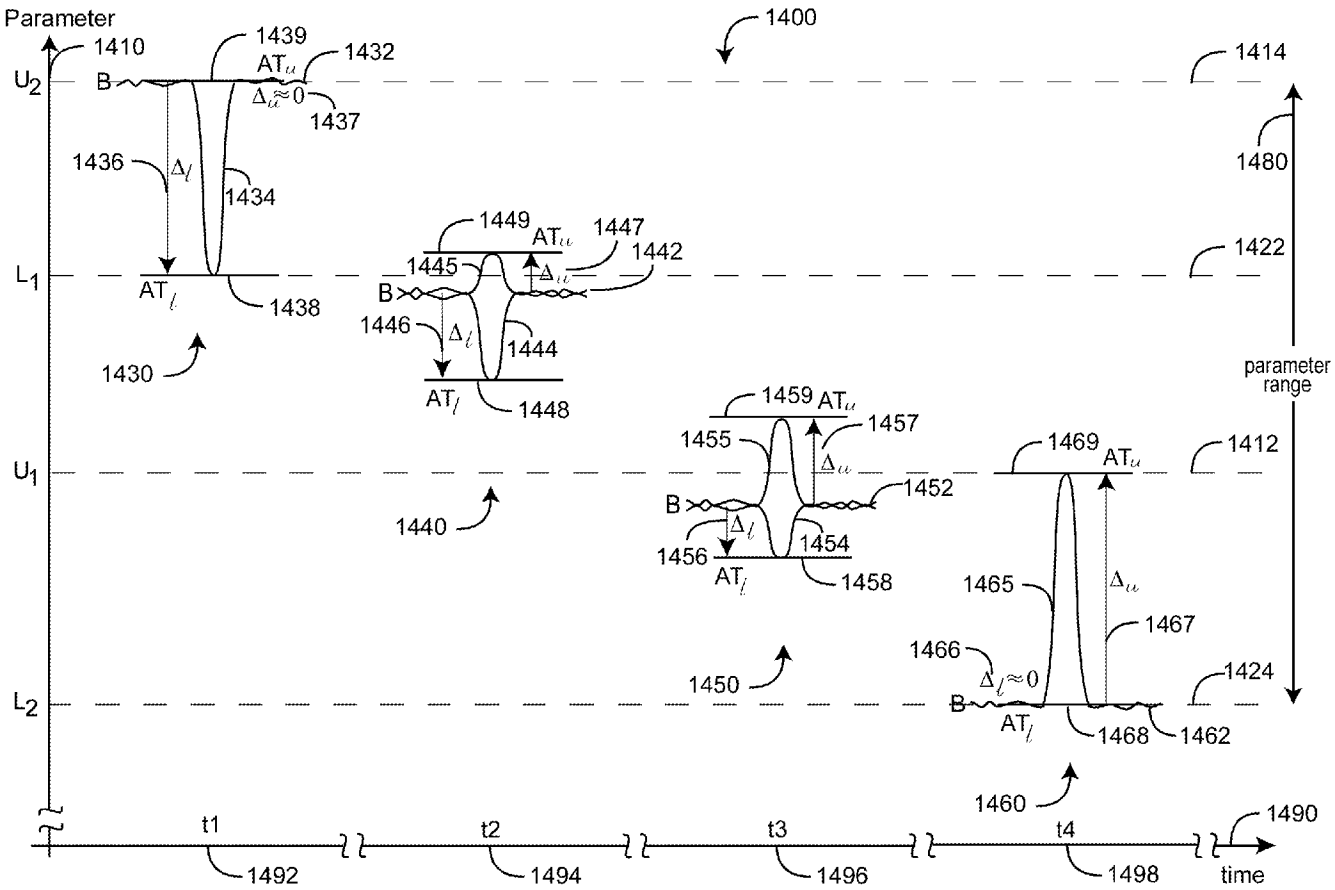
FIG. 14 is an exemplar graph of a physiological parameter versus time illustrating an adaptive alarm system having both lower and upper alarm limits.

FIGS. 14A-B illustrate the operational characteristics an adaptive alarm system 1200 (FIGS. 12A-B) having upper limits $U_1$, $U_2$ 1412, 1414 and lower limits $L_1$, $L_2$ 1422, 1424. An alarm 1212 (FIG. 12A) output is responsive to a baseline (B) 1432, 1442, 1452, 1462; an upper delta ($\Delta_u$) 1437, 1447, 1457, 1467; and a corresponding upper adaptive threshold ($AT_u$) 1439, 1449, 1459, 1469, according to EQS. 9-10, above. Further, the alarm 1212 (FIG. 12A) output is responsive to a lower delta ($\Delta_l$) 1436, 1446, 1456, 1466 and a corresponding lower adaptive threshold ($AT_l$) 1438, 1448, 1458, 1468, according to EQS. 11-12, above.

As shown in FIGS. 14A-B, a physiological parameter 1410 is graphed versus time 1490 for various time segments $t_1$, $t_2$, $t_3$, $t_4$ 1492-1498. The parameter range (PR) 1480 is:

$$PR=U_2-L_2 \tag{13}$$

the lower adaptive threshold $AT_l$ range is:

$$ATR_l=L_1-L_2 \tag{14}$$

the upper adaptive threshold $AT_U$ range is:

$$ATR_l=U_2-U_1 \tag{15}$$

As shown in FIG. 14A, during a first time period $t_1$ 1492, a parameter segment 1430 has a baseline (B) 1432 at about $U_2$ 1414. As such, $\Delta_l$ 1436=$U_2-L_1$; $\Delta_u$ 1437=0; $AT_l$ 1438=$L_1$; $AT_u$ 1439=$U_2$. Accordingly, a negative transient 1434 having a size less than $U_2-L_1$ does not trigger an alarm.

Also shown in FIG. 14A, during a second time period $t_2$ 1494, a parameter segment 1440 has a baseline (B) 1442 less than $U_2$. As such, $\Delta_l$ 1446 is less than $U_1-L_1$ and the adaptive threshold ($AT_u$) 1447 is between $U_1$ and $U_2$. Accordingly, a smaller negative transient 1444 will trigger the alarm as compared to the negative transient 1434 in the first time segment 1430.

Further shown in FIG. 14A, during a third time period $t_3$ 1496, a parameter segment 1450 has a baseline (B) 1452 less than $U_1$ 1412. As such, a smaller negative transient 1454 will trigger the alarm as compared to the negative transient 1444 in the second time segment 1440. However, a larger positive transient 1455 is needed to trigger the alarm as compared to the positive transient 1445 in the second time segment 1440.

Additionally shown in FIG. 14A, during a fourth time period $t_4$ 1460, a parameter segment 1460 has a baseline (B) 1462 at about $L_2$ 1424. As such, $\Delta_l$ 1466=0; $\Delta_u$ 1467=$U_1-L_2$; $AT_l$ 1468=$L_2$; $AT_u$ 1469=$U_1$. Accordingly, a positive transient 1465 having a size less than $U_1-L_2$ does not trigger an alarm.

An adaptive alarm system has been disclosed in detail in connection with various embodiments. These embodiments are disclosed by way of examples only and are not to limit the scope of the claims that follow. One of ordinary skill in the art will appreciate many variations and modifications.

What is claimed is:

[1. A system for reducing electronic alarms in a medical patient monitoring system, the system comprising:

an optical sensor configured to transmit optical radiation into a tissue site of a patient and detect attenuated optical radiation indicative of at least one physiological parameter of a patient; and one or more hardware processors in electronic communication with the optical sensor, the one or more hardware processors configured to:

measure oxygen saturation values of a patient over a first period of time;

determine if at least one oxygen saturation value obtained over the first period of time exceeds a first alarm threshold;

determine whether a first alarm should be triggered based on the determination that the at least one oxygen saturation value obtained over the first period of time exceeds the first alarm threshold;

determine a second alarm threshold to be applied during a second period of time subsequent to the first period of time, the second alarm threshold replacing the first alarm threshold, the second alarm threshold being determined by:

comparing at least a first oxygen saturation value obtained during the first time period with a lower limit associated with oxygen saturation; and computing a second alarm threshold based on the comparison where the second alarm threshold is computed to be at a value less than the at least first oxygen saturation value and greater than the lower limit and at an offset from the first oxygen saturation value, wherein the offset is configured to diminish as a difference between the at least first oxygen saturation value and the lower limit diminishes;

measure oxygen saturation values of a patient over the second period of time to determine at least a second oxygen saturation value; and determine whether a second alarm should be triggered by determining if at least one oxygen saturation value obtained during the second period of time exceeds the second alarm threshold and triggering an alarm if it is determined the second alarm should be triggered.]

[2. The system of claim 1, wherein the one or more hardware processors are configured to calculate a first baseline measurement from the measured oxygen saturation values over the first period of time and wherein the at least one oxygen saturation value obtained during the first period of time corresponds to the first baseline measurement.]

[3. The system of claim 2, wherein the one or more hardware processors are configured to calculate a second baseline measurement from the measured oxygen saturation values over the second period of time and wherein the at least one oxygen saturation value obtained during the second period of time corresponds to the second baseline measurement.]

[4. The system of claim 1, wherein the lower limit is predefined and corresponds to a minimum parameter value for oxygen saturation.]

[5. The system of claim 1, wherein the one or more hardware processors are further configured to wait for a time delay prior to the triggering of the second alarm, and wherein the time delay is a function of the second alarm threshold.]

[6. The system of claim 5, wherein the time delay decreases as the difference between the at least first oxygen saturation value and the lower limit diminishes.]

[7. The system of claim 1, wherein the first alarm threshold is predetermined.]

[8. A system for reducing electronic alarms in a medical patient monitoring system including a pulse oximeter in communication with an optical sensor, the system comprising one or more hardware processors configured to:

measure oxygen saturation values of a patient over a first period of time;

determine if at least one oxygen saturation value obtained over the first period of time exceeds a first alarm threshold;

determine whether a first alarm should be triggered based on the determination that the at least one oxygen saturation value obtained over the first period of time exceeds the first alarm threshold;

compare at least a first oxygen saturation value obtained during the first time period with a lower limit associated with oxygen saturation;

compute a second alarm threshold based on the comparison;

determine a time delay based on the computed second alarm threshold, wherein the time delay approaches zero as the first oxygen saturation value approaches the lower limit;

measure oxygen saturation values of a patient over the second period of time to determine at least a second oxygen saturation value; and determine whether a second alarm should be triggered by determining if at least one oxygen saturation value obtained during the second period of time exceeds the second alarm threshold for the time delay and triggering an alarm if it is determined the second alarm should be triggered.]

[9. The system of claim 8, wherein the first alarm threshold is predetermined.]

[10. The system of claim 8, wherein the lower limit is predefined and corresponds to a minimum parameter value for oxygen saturation.]

[11. The system of claim 8, where the second alarm threshold is computed to be at a value less than the at least first oxygen saturation value and greater than the lower limit and at an offset from the first oxygen saturation value, wherein the offset is configured to diminish as a difference between the at least first oxygen saturation value and the lower limit diminishes.]

[12. An electronic method for reducing electronic alarms in a medical patient monitoring system, the electronic method comprising:

measuring oxygen saturation values of a patient over a first period of time;

determining if at least one oxygen saturation value determined over the first period of time exceeds a first alarm threshold;

determining whether a first alarm should be triggered based on the determination that at least one oxygen saturation value obtained during the first period of time exceeds the first alarm threshold;

comparing at least a first oxygen saturation value obtained during the first time period with a lower limit associated with oxygen saturation;

computing the second alarm threshold based on the comparison where the second alarm threshold is computed to be at a value less than the at least first oxygen saturation value and greater than the lower limit and at an offset from the first oxygen saturation value, wherein the offset is configured to diminish as a difference between the at least first oxygen saturation value and the lower limit diminishes and wherein the second alarm threshold is configured to be applied during a second period of time subsequent to the first period of time, the second alarm threshold replacing the first alarm threshold;

measuring oxygen saturation values of a patient over the second period of time to determine at least a second oxygen saturation value; and determining whether a second alarm should be triggered by determining if at least one oxygen saturation value obtained during the second period of time exceeds the second alarm threshold and triggering an alarm if it is determined the second alarm should be triggered.]

[13. The electronic method of claim 12, wherein the one or more hardware processors are configured to calculate a first baseline measurement from the measured oxygen saturation values over the first period of time and wherein the at least one oxygen saturation value obtained during the first period of time corresponds to the first baseline measurement.]

[14. The electronic method of claim 13, wherein the one or more hardware processors are configured to calculate a second baseline measurement from the measured oxygen saturation values over the second period of time and wherein the at least one oxygen saturation value obtained during the second period of time corresponds to the second baseline measurement.]

[15. The electronic method of claim 12, wherein the lower limit is predefined and corresponds to a minimum parameter value for oxygen saturation.]

[16. The electronic method of claim 12, wherein the one or more hardware processors are further configured to wait for a time delay prior to the triggering of the second alarm, and wherein the time delay is a function of the second alarm threshold.]

[17. The electronic method of claim 16, wherein the time delay decreases as the difference between the at least first oxygen saturation value and the lower limit diminishes.]

[18. The electronic method of claim 12, wherein the first alarm threshold is predetermined.]

*19. A system for reducing electronic alarms in a patient monitoring system, the system comprising:*

*an optical sensor configured to transmit optical radiation into a tissue site of a patient and detect attenuated optical radiation indicative of an oxygen saturation of a patient; and*

*one or more hardware processors in electronic communication with the optical sensor, the one or more hardware processors configured to:*

*determine, over a first period of time, whether a first alarm should be triggered based on a first oxygen saturation value obtained in the first period of time crossing a first alarm limit;*

*access a second alarm limit to be applied during a second period of time subsequent to the first period of time, the second alarm limit replacing the first alarm limit, wherein the second alarm limit has a value less than the first oxygen saturation value and greater than a lower limit and at an offset from the first oxygen saturation value, wherein the offset decreases as a difference between the first oxygen saturation value and the lower limit diminishes;*

*determine oxygen saturation values of the patient over the second period of time; and*

*trigger a second alarm based on at least one value of the oxygen saturation values obtained over the second period of time crossing the second alarm limit.*

*20. The system of claim 19, wherein the difference diminishes in response to a decrease in the patient's oxygen saturation until it reaches zero.*

*21. The system of claim 20, wherein the diminishment is proportional to the difference.*

*22. The system of claim 20, wherein the diminishment is a stepwise function of discrete diminishment steps.*

*23. The system of claim 19, wherein the system automatically determines the second alarm limit.*

*24. The system of claim 19, wherein the system automatically determines the first alarm limit.*

*25. The system of claim 19, wherein the lower limit is predetermined and corresponds to a minimum parameter value for oxygen saturation.*

*26. The system of claim 19, wherein the one or more hardware processors are further configured to wait for a time delay prior to triggering of the second alarm, and wherein the time delay is a function of the second alarm limit.*

*27. An electronic method of reducing electronic alarms in a patient monitoring system, the electronic method comprising:*

*determining, over a first period of time, whether a first alarm should be triggered based on a first oxygen saturation value obtained in the first period of time crossing a first alarm limit;*

*accessing a second alarm limit to be applied during a second period of time subsequent to the first period of time, the second alarm limit replacing the first alarm limit, wherein the second alarm limit has a value less than the first oxygen saturation value and greater than a lower limit and at an offset from the first oxygen saturation value, wherein the offset decreases as a difference between the first oxygen saturation value and the lower limit diminishes;*

*determining oxygen saturation values of the patient over the second period of time; and*

*triggerring a second alarm based on at least one value of the oxygen saturation values obtained over the second period of time crossing the second alarm limit.*

*28. The electronic method of claim 27, wherein the difference diminishes in response to a decrease in the patient's oxygen saturation until it reaches zero.*

*29. The electronic method of claim 28, wherein the diminishment is proportional to the difference.*

*30. The electronic method of claim 28, wherein the diminishment is a stepwise function of discrete diminishment steps.*

*31. The electronic method of claim 27, further comprising automatically determines the second alarm limit.*

*32. The electronic method of claim 27, further comprising automatically determines the first alarm limit.*

*33. The electronic method of claim 27, wherein the lower limit is predetermined and corresponds to a minimum parameter value for oxygen saturation.*

*34. The electronic method of claim 27, further comprising waiting for a time delay prior to triggering of the second alarm, and wherein the time delay is a function of the second alarm limit.*

*35. A system for reducing electronic alarms in a patient monitoring system, the system comprising one or more hardware processors configured to:*

*determine, over a first period of time, whether a first alarm should be triggered based on a first oxygen saturation value obtained in the first period of time crossing a first alarm limit;*

*access a second alarm limit to be applied during a second period of time subsequent to the first period of time, the second alarm limit replacing the first alarm limit, wherein the second alarm limit has a value less than the first oxygen saturation value and greater than a lower limit and at an offset from the first oxygen saturation value, wherein the offset decreases as a difference between the first oxygen saturation value and the lower limit diminishes;*

*determine oxygen saturation values of the patient over the second period of time; and*

*trigger a second alarm based on at least one value of the oxygen saturation values obtained over the second period of time crossing the second alarm limit.*

* * * * *